Figure 1:
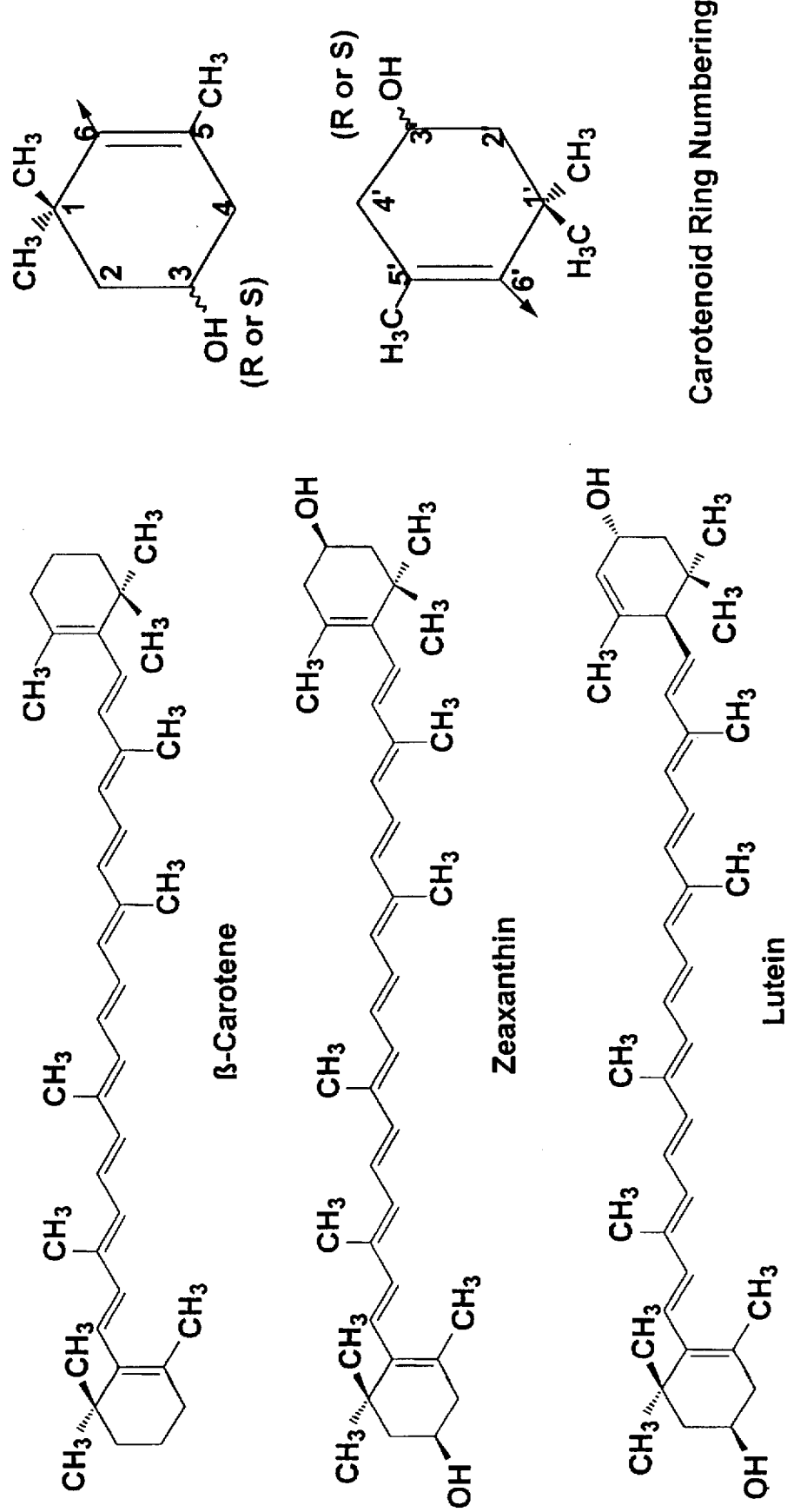
Figure 2:
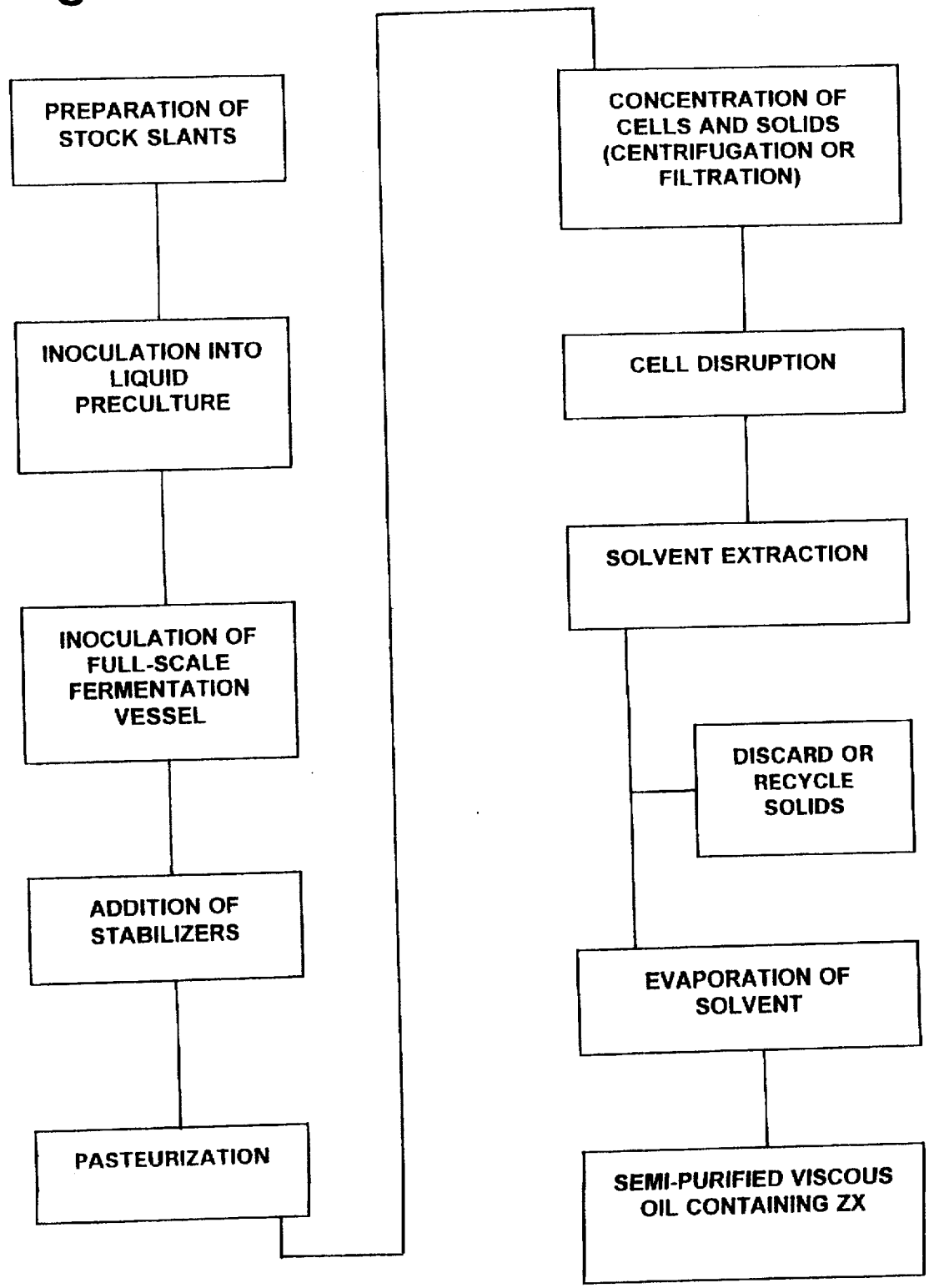

United States Patent [19]
Garnett et al.

[11] Patent Number: 5,747,544
[45] Date of Patent: May 5, 1998

[54] METHOD OF USING PURE 3R-3'R STEREOISOMER OF ZEAXANTHIN TO TREAT OR PREVENT RETINAL DEGENERATION IN HUMANS

[75] Inventors: Kevin M. Garnett, St. Louis; Dennis L. Gierhart, High Ridge; Luis H. Guerra-Santos, Ballwin, all of Mo.

[73] Assignee: Applied Food Biotechnology, Inc., O'Fallon, Mo.

[21] Appl. No.: 550,665

[22] Filed: Oct. 31, 1995

[51] Int. Cl.$^6$ ................................................. A61K 31/045
[52] U.S. Cl. ........................................................ 514/729
[58] Field of Search ............................................ 514/729

[56] References Cited

U.S. PATENT DOCUMENTS

| | | | |
|---|---|---|---|
| 3,841,967 | 10/1974 | Dasek et al. | 195/29 |
| 3,891,504 | 6/1975 | Schocher et al. | 195/28 R |
| 3,951,743 | 4/1976 | Shepherd et al. | 195/28 R |
| 4,153,615 | 5/1979 | Saucy | 260/340.9 R |
| 4,522,743 | 6/1985 | Horn et al. | 252/311 |
| 4,726,955 | 2/1988 | Horn et al. | 426/73 |
| 4,851,339 | 7/1989 | Hills | 435/67 |
| 4,952,716 | 8/1990 | Lukac et al. | 556/482 |
| 5,180,747 | 1/1993 | Matsuda et al. | 514/681 |
| 5,227,507 | 7/1993 | Lukac et al. | 556/449 |
| 5,308,759 | 5/1994 | Gierhart | 435/67 |
| 5,310,764 | 5/1994 | Baranowitz et al. | 514/725 |
| 5,350,773 | 9/1994 | Schweikert et al. | 514/763 |
| 5,356,636 | 10/1994 | Schneider et al. | 424/489 |
| 5,382,714 | 1/1995 | Khachik | 568/834 |
| 5,427,783 | 6/1995 | Gierhart | 424/93.4 |
| 5,429,939 | 7/1995 | Misawa et al. | 435/67 |
| 5,523,494 | 6/1996 | Torres-Cardona et al. | 568/834 |
| 5,527,533 | 6/1996 | Tso et al. | 424/422 |

FOREIGN PATENT DOCUMENTS

96/40092  12/1996  WIPO .

OTHER PUBLICATIONS

Bendich, A., et al, "Biological actions of carotenoids," *FASEB Journal* 3: 1927–1932 (1989).

Blumenkranz, M.S., et al, "Risk factors in age–related maculopathy complicated by choroidal neovascularization," *Ophthalmology* 93: 552–558 (1986).

Bone, R.A., et al, "Preliminary identification of the human macular pigment," *Vision Res.* 25: 1531–1535 (1985).

Bone, R.A., et al, "Stereochemistry of the macular carotenoids," *Invest. Ophthalmol. Vis. Sci.* 34: 2033–2040 (1993).

Bone, R.A., et al, "Distribution of macular pigment stereomers in individual eyes, including those with age–related macular degeneration," abstract, *ARVO Abstracts Investig. Ophthalmol. Visual Science* 35: 1502 (1994).

Christen, W.G., "Antioxidants and Eye Disease," *Amer. J. Medicine* 97 (suppl. 3A): 14S–17S (1994).

Columbo, V.E., et al, "Structures and properties of stabilized vitamin and carotenoid dry powders," *Food Structure* 10: 161–170 (1991).

di Mascio, P., et al, "Lycopene as the most efficient biological carotenoid singlet oxygen quencher," *Archives of Biochemistry and Biophysics* 274: 532–538 (1989).

di Mascio, P., et al, "Antioxidant defense systems: the role of carotenoids, tocopherols, and thiols," *Am. J. Clin. Nutr.* 53: 194S–200S (1991).

Dorey, C.K., et al, "Lipofuscin in aged and AMD eyes," in *Retinal Degeneration* (Hollyfield et al, editors, Plenum Press, New York, 1993).

Eye Disease Case–Control Study Group, "Antioxidant status and neovascular age–related macular degeneration," *Arch. Ophthalmol.* 11: 104–109 (1993).

Eye Disease Case–Control Study Group, "Risk factors for neovascular age–related macular degeneration," *Arch. Ophthalmol.* 10: 1701–1708 (1992).

Gerster, H., "Review: antioxidant protection of the ageing macula," *Age and Aging* 20: 60–69 (1991).

Goldberg, J., et al, "Factors associated with age–related macular degeneration," *Amer. J. Epidemiology* 128: 700–710 (1988).

Haegerstrom–Portnoy, G., "Short–wavelength–sensitive–cone sensitivity loss with aging: a protective role for macular pigment?," *J. Opt. Soc. Am.* A5: 2140–2144 (1988).

Handelman, G.J. and Dratz, E.A., "The role of antioxidants in the retina and retinal pigment epithelium and the nature of prooxidant–induced damage," *Adv. Free Radical Biology & Medicine* 2: 1–23 and 55–57 (1986).

Handelman, G.J., et al, "Carotenoids in the human macula and whole retina," *Invest. Ophthalmol. Vis. Sci.* 29: 850–855 (1988).

Malinow, M.R., et al, "Diet–related macular anomalies in monkeys," *Invest. Ophthalmol. Vis. Sci.* 19: 857–863 (1980).

(List continued on next page.)

Primary Examiner—William R.A. Jarvis
Attorney, Agent, or Firm—Patrick D. Kelly

[57] ABSTRACT

A method is disclosed for treating or preventing macular degeneration, one of the leading causes of blindness and vision loss, by administering a preparation of zeaxanthin which contains the 3R-3'R stereoisomer as a sole or heavily dominant stereoisomer. Zeaxanthin, a yellowish pigment which is naturally present in macular cells in the center of the human retina, absorbs blue and near-ultraviolet light radiation, thereby protecting retinal cells against phototoxic damage. The purified R-R isomer of zeaxanthin can be taken orally as a prescription drug by patients suffering from macular degeneration, and it can also be used as a nutritional supplement, in forms such as a vitamin pills or food additives, by anyone who wants to reduce his or her risk of macular degeneration, which is widespread among people over the age of about 50 or 60. Zeaxanthin preparations which contain only the desired R-R isomer can be produced by fermentation of *Flavobacterium multivorum* cells (ATCC accession number 55238) or other host cells which contain genes isolated from this *F. multivorum* strain. These bacterial cells do not create any detectable quantities of the undesired S-S or S-R isomers of zeaxanthin, and they do not synthesize significant quantities of other carotenoids which might compete against zeaxanthin for alimentary uptake after oral ingestion.

14 Claims, 2 Drawing Sheets

OTHER PUBLICATIONS

Mares–Perlman, J.A., et al, "Serum antioxidants and age-related macular degeneration in a population-based case-control study," *Arch. Ophthalmol.* 113: 1518–1523 (1995).

National Advisory Eye Council, *Vision Research Research: A National Plan, 1994–1998* (NIH Publication 93-3186), pp. 55–64, 336, and 356 (1993).

Seddon, J.M., et al, "Dietary carotenoids, vitamins A, C, and E, and advanced age-related macular degeneration," *JAMA* 272: 1413–1420 (1994).

Sperduto, R.D., et al, "Do we have a nutritional treatment for age-related cataract or macular degeneration?," *Arch. Ophthalmol.* 108: 1403–1405 (1990).

Taylor, A., et al, "Oxidation and aging: impact on vision," *Journal of Toxicology and Industrial Health* 9: 349–371 (1993).

West, S., et al, "Are antioxidants or supplements protective for age-related macular degeneration?" *Arch. Ophthalmol.* 112: 222–227 (1994).

METHOD OF USING PURE 3R-3'R STEREOISOMER OF ZEAXANTHIN TO TREAT OR PREVENT RETINAL DEGENERATION IN HUMANS

BACKGROUND OF THE INVENTION

This invention is in the field of biochemistry, and relates to the creation and purification of a certain isomer of a carotenoid pigment called zeaxanthin (abbreviated as ZX), for use in preventing or treating macular degeneration, a disease which damages retinal tissue and causes blindness.

The retina is the tissue that lines the internal portion of the back of the eyeball. After light enters the eye through the cornea, it passes through a focusing lens, which is surrounded by a clear fluid known as the vitreous humor. The light then strikes the retina and activates a photosensitive chemical called rhodopsin, which is located in the rod and cone cells that line the retina. The activation of rhodopsin (and certain other closely related chemicals which have different wavelength sensitivities) by light triggers a series of biochemical reactions that generate nerve impulses, which are sent to the brain for processing into sight and vision.

The structures, cellular anatomy, and biochemistry of retinal neurons are described and illustrated in numerous texts on human physiology; for example, a good overview is provided in *Guyton's Textbook of Medical Physiology*. More detail is provided in various medical school texts that focus specifically on the eye and diseases of the eye, such as Gittinger 1988, and Vaughn and Asbury 1992 (complete citations to all books and articles are provided below, before the claims).

The neuronal structures and biochemistry of the retina are extremely complicated; for example, in most locations, the retina contains at least a dozen distinct layers. Light which reaches the retina initially passes through the inner limiting membrane (which separates the liquid vitreous humor from the retinal cell fluids), then it passes through the stratum opticum (which contains the nerve fibers that carry signals from the rods and cones to the main optic nerve), a layer of ganglionic cells, inner and outer plexiform and nuclear layers, an outer limiting membrane, and the layer of rods and cones, often referred to collectively as photoreceptors. Beyond the layer of rods and cones is a pigmented layer, often called the retinal pigmented epithelium (RPE), which contains the dark pigment melanin, which absorbs light to prevent it from reflecting back into the eye. The RPE cells carry on an active process of phagocytosis, in which they dissolve and digest the detritus created by the rapid turnover and renewal of the rod and cone cells.

The outer (posterior) side of the RPE layer is attached to a structure called the Bruch's membrane, which is a non-cellular matrix that allows oxygen and nutrients to diffuse into RPE cells and which also allows metabolic wastes to diffuse out of the RPE and be carried away. On the other side of the Bruch's membrane is a dense bed of capillaries called the choriocapillaris. Beyond and outside that layer of capillaries is the sclera, which is the relatively rigid structural enclosure that holds the eyeball in a roughly spherical shape.

Over most of the retina, light must pass through the multiple layers of nerve cells and fibers before it can reach the rods and cones which convert the incoming light energy into nerve signals. This rather curious arrangement was caused by evolution rather than logic, and the interfering cellular layers cause a significant loss in visual acuity in those portions of the retina where this arrangement occurs.

However, in a small circular region called the fovea, which is located in the very center of the retina and which is less than half a millimeter in diameter, there are no nerve fibers or cells which lie in the path of the incoming light before the light reaches the cone photoreceptors. This causes the cones to be exposed to incoming light in a much more direct manner, with less cellular blockage and interference before the light reaches the photoreceptors.

The fovea sits in the middle of a somewhat larger circular region called the macula, which is usually about 2 to 3 millimeters in diamater, and which has two characteristics that distinguish it from the surrounding retinal tissue. First, the macula contains relatively fewer rods than cones, compared to the remainder of the retina (in the fovea, at the very center of the macula, there are no rods at all). And second, the macula is distinguished by a yellow color, caused by two yellow-colored carotenoid pigment molecules called lutein and zeaxanthin. The chemistry of these carotenoid pigments is discussed below, under a separate subheading. Before these carotenoid molecules are discussed, the following section provides an overview of several retinal disease conditions that are collectively known as macular degeneration.

Macular Degeneration; Drusen and Lipofuscin

Millions of Americans suffer from various types of retinal disease or damage that are collectively called macular degeneration. In general, macular degeneration refers to any condition that involves progressive damage to or deterioration of the retinal cells or structures in the macular region of the retina.

There are several distinct types of macular degeneration. The most common type is usually referred to as age-related macular degeneration, which is abbreviated herein and in most scientific publications by the acronym AMD. Some articles use the acronym ARMD, which refers to the same condition. Also, some articles refer to age-related maculopathy, which involves the early stages of macular damage, and which does not imply severe damage.

AMD affects almost 30% of Americans over the age of 65, and it is the leading cause of new blindness among the elderly. AMD can cause any level of visual impairment, ranging from only a slight deterioration of peripheral vision, to total blindness (defined as the inability to distinguish any light).

There are two forms of AMD, often referred to as the "wet" (or "exudative") form, and the "dry" form. The wet form involves aggressive growth of new blood vessels into retinal tissue, to a point where the encroaching blood vessels (or fluids exuded by such blood vessels) disrupt and destroy the proper organization of the retinal layers. This abnormal blood vessel growth is often called neovascularization. Although wet AMD can sometimes be treated by using a laser to ablate (close off) the newly forming blood vessels, laser treatment can only retard blood vessel growth for a while, and it usually cannot prevent the eventual loss of almost all vision; wet AMD almost always leads eventually to total or nearly-total blindness. Fortunately, the wet form occurs in only a minority (about 5 to 10 percent) of patients suffering from AMD.

The other form of AMD, which occurs in more than 90% of all cases, is often called "dry" or non-exudative AMD; since it is so prevalent, it is often referred to simply as AMD, and all references herein to AMD refer to the dry form of AMD, which does not involve aggressive blood vessel growth. This form of AMD is characterized by a slow and gradual atrophy of photoreceptors and the retinal pigmented epithelial (RPE) layer in the macula. Although this form of AMD hardly ever leads to total blindness, it often leads to severe damage to a patient's sight and depth perception, and renders a patient unable to read or distinguish well-known objects such as the faces of friends or relatives. As such, it leads to debilitating forms of functional blindness, and often renders patients unable to drive or to walk safely across streets, sidewalks, and other public places, and unable to carry out the typical chores and interactions that are required for normal activity in the outside world.

In addition to these forms of age-related macular degeneration, there are a number of diseases that involve macular degeneration as one of their main symptoms. Such diseases include Stargardt's disease, Best's disease, Batten's disease, Sjogren-Larsson syndrome, cone-rod dystrophy, and ovine ceroid lipofuscinosis (articles describing each of these diseases are cited on page 5 of Dorey et al 1993). In addition, still other diseases which involve lysosomal storage problems are also correlated with macular degeneration. Many of these diseases are known to have genetic components, as evidenced by familial patterns of inheritance; some of the defective genes which lead to these diseases have been fully isolated, and genetic screening tests can indicate whether a person has the defective gene. Any person who has or is at substantial risk of having such a defective gene, as evidenced by genetic testing or a family history of such problems, should be regarded as being at substantial risk of macular degeneration; subject to the guidance of a physician, such people probably would benefit from taking a zeaxanthin formulation as described herein, as a precautionary measure even if no onset of symptoms has been observed.

By robbing them of their eyesight in a gradual but relentless manner, macular degeneration inflicts enormous physiological and psychological suffering on its victims. It also costs American society billions of dollars each year, both in direct loss of economic productivity among people who have lost or are losing their eyesight, and in the heavy indirect costs imposed on family members, insurance providers, social agencies, and others who must provide or help pay for health care, living assistance, transportation, and other special accomodations for people who suffer from functional blindness or other severe damage to their eyesight.

In view of the enormous personal, social, and economic burdens of macular degeneration, researchers and physicians have been searching for more than fifty years for ways to effectively treat or prevent blindness and other vision loss caused by macular degeneration. However, despite all of their efforts for more than half a century, no effective treatments are available today.

Macular degeneration is usually diagnosed by ophthalmologists or other physicians, by means of special photographs of the retina. These photographs are often called "fundus" photos. In a typical diagnostic procedure, a physician dilates the patient's pupil's, and injects a fluorescent dye (such as fluorescein) into a patient's blood. The physician then takes a series of magnified photographs (called angiograms) of the retina, using a blue light source with a wavelength that causes the drug in the patient's blood to emit fluorescent light at a different wavelength. The physician then analyzes the series of photographs of the retina to determine the presence and concentration of either or both of two types of cellular debris, described below. If present at abnormal levels, these forms of cellular debris indicate the presence or early onset of macular degeneration. A good cross-sectional illustration of both of these types of cellular debris and damage are provided in Taylor et al 1993.

One of these types of cellular debris, which has been known and studied for several decades, is called drusen. Drusen (this is the plural form; the singular noun, which refers to one particle, is "druse") in two distinct forms. A small quantity of hard drusen (comprising small, discrete particles) is usually present in the eyes of nearly anyone over about 40 years old. Unless present at abnormal levels, hard drusen do not indicate retinal damage. In order to provide a quantifiable boundary between hard drusen and soft drusen, hard drusen are usually defined to include drusen deposits with a diameter of less than 63 micrometers (Dorey et al 1993).

By contrast, a significant quantity of soft drusen deposits, with diameters of more than 63 µm, indicates that substantial retinal damage has occurred or at least commenced. A patient whose retinal tissue contains a significant quantity of soft drusen is usually regarded as suffering from macular degeneration.

If only a small number of soft drusen are observed during visual examination, the patient is usually classified as suffering from an "early onset" stage of macular degeneration. Some degree of loss of peripheral vision is usually detectable in patients at this stage. Larger number of soft drusen indicate more extensive macular deterioration, and in patients suffering from complete blindness caused by advanced macular degeneration, the retinal layers in the macula are often severely disfigured due to the swelling caused by large, amorphous masses of soft drusen which have disrupted and disorganized the retinal layers by pushing the dark (melanin-pigmented) layer of retinal pigmented epithelium (RPE) away from the Bruch's membrane and capillary bed. This type of intrusion and displacement disrupts the flow of fresh nutrients from the capillaries into the RPE, and the removal of waste metabolites from the RPE by the capillaries.

The other type of cellular debris that is usually present in the retinas of patients suffering from macular degeneration is called lipofuscin. Lipofuscin has not been recognized for long as an indicator of AMD, and most ophthalmologists currently do not have equipment designed to measure it. Although several prior articles (e.g., Weiter et al 1988) had noticed certain correlations between lipofuscin and AMD, a direct showing that lipofuscin levels can be used as an indicator of AMD, using non-invasive diagnostic methods rather than retinal biopsy after death, did not appear until Dorey et al 1993, which described equipment and methods for evaluating lipofuscin in living patients.

Age-related and other forms of macular degeneration are described in more detail in numerous articles and texts, including Taylor 1993, Gittinger 1988, and Vaughan and Asbury 1992.

Carotenoid Chemistry

The term "carotenoids" refers to a large class of molecules (more than 600 naturally occurring carotenoids have been identified) which have several relevant characteristics, including the following:

1. Chemically, carotenoids are classified as "polyisoprenoid" molecules. This means that they are synthesized by reactions which involve coupling together molecules of isoprene (also called isopentenyl), an unsaturated 5-carbon molecule. Because this building block contains 5 carbon atoms, most carotenoids and carotenoid precursors contain multiples of 5 carbon atoms. In one common carotenoid synthesis pathway, farnesyl (a 15-carbon precursor, formed from 3 molecules of isoprene) is converted into geranylgeranyl (with 20 carbon atoms) by adding another isoprene block. In the next step, two molecules of geranylgeranyl are coupled together to form phytoene, a 40-carbon carotenoid. Phytoene is then converted into lycopene, another 40-carbon carotenoid, by removing some of the hydrogen atoms coupled to the carbon atoms, and increasing the number of unsaturated bonds between the carbon atoms. Lycopene is then converted into β-carotene, another 40-carbon carotenoid, by forming ring structures at both ends of the lycopene chain.

2. Carotenoids have multiple unsaturated bonds. This allows them to absorb high-energy light waves in the blue and near-ultraviolet regions of the spectrum.

3. Because they absorb wavelengths in the blue and near-UV regions of the spectrum while reflecting off wavelengths in other regions of the spectrum, carotenoids usually have yellow, orange, brown, or red colors. The name "carotenoid" derives from carrots; the first known carotenoids were identified as the pigments that give carrots an orange color. Exact colors caused by carotenoids in liquid solutions depend on various factors, including concentration, specific molecular structures of different carotenoids, and the presence of other chemicals in a mixture that contains a carotenoid.

4. Carotenoids have "conjugated" double bonds. This term indicates that the double bonds alternate with single bonds, so that each carbon atom in a chain is double-bonded to one other carbon atom, but no carbons are double-bonded to two other carbons. This arrangement can be understood by considering FIG. 1, which shows the structures of β-carotene, zeaxanthin, and lutein.

Different carotenoids have different levels of conjugation. As an illustration, in all three of the carotenoids shown in FIG. 1, the entire straight chain portion of each molecule is conjugated, with alternating double and single bonds. In β-carotene and zeaxanthin, the conjugation extends to the first bonds in both end rings. By contrast, lutein has a lower conjugation level, since the double bond in one of its end rings does not have the proper placement for complete conjugation. Zeaxanthin and lutein have identical chemical formulas; the only difference between them is in the location of the double bond in one (but not both) of the end rings. It should also be noted that a different carotenoid called lycopene, the most highly conjugated of all carotenoids, is the best singlet oxygen quencher of all known carotenoids (di Mascio et al 1989). This further illustrates the direct correlation between conjugation levels and protective activity.

Because carotenoids are designed and selected (through evolutionary development) to absorb the potentially harmful energy of blue and near-UV light, they are used as protective pigments by both plants and animals. They are found extensively throughout the plant kingdom, since one of the functional goals of most plants is to absorb as much sunlight as possible while minimizing cellular and DNA damage caused by blue, ultraviolet, and near-ultraviolet radiation. Ultraviolet radiation damage to plants is a major problem, and carotenoids can help minimize it; in human retinas, UV radiation is usually not a severe problem, because it is absorbed by the lens inside the eyeball before reaching the retina.

Because carotenoid molecules are ideally suited for protecting cells and DNA against phototoxic damage, animals have also acquired (through evolution) ways to utilize carotenoids as photo-protective pigments. Since animals cannot synthesize carotenoids in their bodies, they must ingest carotenoids (or carotenoid precursors) from plant sources. β-carotene is a widely-known example; mammalian cells cannot synthesize it, so mammals must obtain it from plant sources, or from meat. Once inside a mammalian body, β-carotene is converted by enzymes into other molecular forms, including Vitamin A (retinol), which is formed by splitting β-carotene into two halves.

Carotenoids are divided into two main classes, carotenes and xanthophylls. Carotenes, such as β-carotene, do not contain any oxygen molecules; they are true hydrocarbons, formed from only carbon and hydrogen. By contrast, xanthophylls (such as zeaxanthin and lutein, shown in FIG. 1) also contain oxygen atoms.

FIG. 1 shows the conventional numbering of the carbon atoms in the left and right end rings of zeaxanthin. By convention, the carbon atoms in the left end ring are numbered 1 through 6, while the carbon atoms in the right end ring are referred to by "prime" numbers, such as the 3' carbon (pronounced "three prime"). Since zeaxanthin is completely symmetrical with regard to the left and right ends, the terms "left" and "right" are merely a convention, used to simplify discussion. However, it should be noted that lutein is not symmetrical; the position of the double bond in the "left" ring is not the same as the placement of the double bond in the "right" ring.

Since zeaxanthin is formed by adding two hydroxy (—OH) groups to β-carotene, its chemical name is dihydroxy-carotene; alternately, some chemists refer to it as carotene-diol. Since the exact placement of the hydroxy groups on the #3 and #3' carbon atoms of the end rings is important, the full chemical name for zeaxanthin is 3,3'-dihydroxy-β-β-carotene. This molecule was given the common name "zeaxanthin" because it was first identified as the pigment which gives corn its yellow color; the scientific name for corn is *Zea mays*.

As noted above, more than 600 naturally-occurring carotenoids have been identified, and several dozen of these are genuinely important in biochemistry and commerce. Zeaxanthin and lutein are especially important in this invention, because they are present in the retinas of mammals and most other animals. Zeaxanthin and lutein are the two primary pigments which give the macula (the circular region in the center of the retina, as discussed above) its characteristic yellow color. Lutein is commercially important; lutein-containing plant extracts (mainly from marigolds) are widely fed to chickens, to give their skin and egg yolks a deeper yellow color, which appeals to grocery shoppers and consumers. Zeaxanthin can accomplish the same result, and is roughly 2–3 times more potent on a per-weight basis than lutein; however, in the past, zeaxanthin sources have been too expensive for use in poultry feeds. U.S. Pat. Nos. 5,308,759 and 5,427,783 (both by Gierhart, and both assigned to Applied Food Biotechnology, Inc., the same company that is the assignee herein) were intended to address the problem of zeaxanthin being too expensive for use in animal feed. These patents relate to using bacterial fermentation to produce zeaxanthin in commercial quantities, so that the zeaxanthin can be fed to poultry and fish for coloring purposes.

Two other carotenoids that are commercially important are lycopene, which is widely used as a red food coloring, and canthaxanthin, which is also used commercially as a red food coloring but to a much lesser extent. Canthaxanthin, which can be chemically synthesized, is deposited in human skin; therefore, some people take it as a tanning agent to cause their skin to become darker. However, the sale of canthaxanthin for tanning purposes is illegal in the United States, since canthaxanthin has been shown to cause retinal maculopathy, a condition which damages the retina and eyesight. Canthaxanthin may displace lutein (the natural pigment in the retinal regions surrounding the macula) in retinal tissue, and it is believed to cause crystal formation which can destroy retinal cells and tissue. Some countries allow the feeding of canthaxanthin to farm-raised fish (mainly salmon and trout), since it can give the flesh of farm-raised fish an appealing darker color. However, the United States does not allow this, because of concern over the fate of canthaxanthin in the retinas of the people who eat farm-raised fish.

Astaxanthin, a red-orange pigment, is another commercially important carotenoid. In nature, salmon obtain it from algae. In commercial fish farming, it is synthesized for salmon feed either chemically, or by a yeast species called *Phaffia rhodoyzyms*. An FDA application by Hoffman-LaRoche, asking for FDA approval to feed synthetic astaxanthin to fish, was held up for nearly 10 years by the U.S. Food and Drug Administration, because the synthetic astaxanthin contained some S-S and S-R stereoisomers (discussed below). The application was eventually approved by the FDA, after the applicant showed that these other stereoisomers exist in nature and are already eaten by fish that are subsequently consumed by humans. That application is available from the FDA under the Freedom of Information Act.

In addition to being synthesized by plants, a number of carotenoids are known to be synthesized by various types of bacteria. Most of these bacteria have evolved in environmental niches that are exposed to direct sunlight, and the carotenoids in such bacteria perform the same type of photo-protective role that carotenoids perform in plants. These bacteria usually generate yellow, orange, or red colonies, and this type of visible pigmentation has made them the subject of analysis to determine the type of pigment they contain. Articles and patents which describe bacterial carotenoids include McDermott et al 1972 and U.S. Pat. No. 5,429,939 (Misawa et al 1995), as well as other articles cited in those two references.

U.S. Pat. No. 5,429,939 (Misawa et al 1995) describes the complete DNA sequences of a number of genes which encode enzymes that are involved in the biosynthesis of a number of types of carotenoids, including zeaxanthin. These genes include:

(1) the crtE gene, which encodes an enzyme that converts farnesyl (a 15-carbon precursor, mentioned above) into geranylgeranyl (a 20 carbon precursor, also mentioned above).

(2) the crtB gene, which encodes an enzyme that couples together two molecules of geranylgeranyl to form phytoene, a 40-carbon carotenoid.

(3) the crtI gene, which encodes an enzyme that removes some of the hydrogen atoms from phytoene to create lycopene.

(4) the crtY gene, which encodes an enzyme that converts lycopene into β-carotene by creating ring structures at the ends of the lycopene molecule.

(5) the crtZ gene, which encodes an enzyme that converts β-carotene into zeaxanthin by adding hydroxyl groups to the #3 carbon atoms on both of the ring structures at the ends of the β-carotene molecule.

(6) the crtX gene, which converts zeaxanthin (a very hydrophobic compound) into a water-soluble molecule called zeaxanthin diglucoside by attaching glucose rings to the zeaxanthin.

As mentioned above, these genes have been fully sequenced, and the relevant DNA and amino acid sequences are listed in published sources such as U.S. Pat. No. 5,429,939 and PCT application WO 91/13078. Various cells containing plasmids which contain these genes have been deposited, by the scientists who created those plasmids, with the American Type Culture Collection (e.g., *Erwinia uredovora* ATCC 19321, and *Erwinia herbicola* ATCC 39368) and with the Fermentation Research Institute in Japan (e.g., *E. coli* FERM BP 2377).

Zeaxanthin Stereochemistry and Isomers

Another aspect of carotenoid chemistry which is very important to the subject invention pertains to a field of chemistry involving "stereochemistry" and "stereoisomers". This topic is explained in detail in any college textbook on organic chemistry. Anyone who works with organic chemistry should already be familiar with the concept of stereoisomers; however, an overview is provided in the following paragraphs, because this issue is of major importance to the subject invention.

Whenever an organic molecule has a carbon atom with four different types of atoms or molecular groups attached to it, that carbom atom is a called a "chiral" carbon atom. In zeaxanthin, the #3 carbon atom and the #3' carbon atom in the two end rings are both chiral atoms, as can be seen by examining FIG. 1.

Whenever a chiral carbon atom is present in an organic molecule, the four different groups which are bonded to that chiral carbon atom can be arranged in either of two spatial arrangements. Since carbon atoms are bonded to other atoms in a three-dimensional tetrahedral arrangement, this can be visualized by assuming or pretending that three of the atoms or groups are attached to the chiral carbon atom in a flat triangular arrangement, which can be drawn on a page. When the arrangement of those three groups is fixed, the fourth group can be attached to the carbon atom (in this type of visualization) in either of two ways: (1) coming up out of the page, toward the reader, which can be indicated in chemical structures by a heavy triangular bond, or (2) going behind the page, away from the reader, usually drawn in chemical structures by dashes or dotted lines.

The two different spatial arrangements of such molecules are called stereoisomers. As discovered in the 1800's by the combined efforts of Jean Baptiste Biot and Louis Pasteur, one of these stereoisomers will rotate polarized light in a "right-handed" manner as the polarized light passes through a liquid solution of the compound. The other arrangement will cause the opposing stereoisomer to rotate polarized light in the opposite "left-handed" manner. The isomer which causes right-handed rotation is called the R stereoisomer (also called the D stereoisomer). The isomer which causes left-handed rotation is called the S stereoisomer (also called the L stereoisomer).

As mentioned above, zeaxanthin has two chiral carbon atoms: one is the #3 carbon atom in the left end ring, while the other is the #3' carbon atom in the right end ring. Therefore, there are four possible stereoisomers of zeaxanthin. One of these stereoisomers is the 3R-3'R isomer, in which the #3 and #3' chiral carbon atoms in both end rings have R configurations. Another stereoisomer is the 3S-3'S isomer, in which the #3 and #3' chiral carbon atoms in both end rings have L configurations. For convenience, these two stereoisomers are referred to herein as the R-R isomer, and the S-S isomer.

The third and fourth isomers are the two "mixed" or "meso" (one R and one S) isomers: the 3R-3'S isomer, and the 3S-3'R isomer. However, since zeaxanthin is symmetric, these two isomers are identical in every respect; if one draws the 3R-3'S isomer on paper, then one merely has to rotate the paper to generate the 3S-3'R isomer. In effect, "meso" isomers are formed by creating either of two stereoisomers (3R-3'S, or 3S-3'R). For this reason, if standard chemical techniques are used to synthesize zeaxanthin, the R-R isomer and the S-S isomer will be present at a concentration of roughly 25% each, while the mixed (meso, S-R) isomer will be present as about 50% of the zeaxanthin. This mixture of all three stereoisomers is called a "racemic" mixture.

The cellular and enzymatic specificities of carotenoids in retinal tissue are extremely precise, and these two types of molecules are not interchangeable. Lutein and zeaxanthin must be regarded as different and distinct carotenoids, each having its own isomers (i.e., stereoisomeric forms). This is true, even though lutein and zeaxanthin might be regarded as isomers of each other under conventional chemical terminology, since they have identical numbers of carbon, hydrogen, and oxygen atoms, in slightly different arrangements.

Since the only isomers that are relevant in carotenoid chemistry are stereoisomers, any reference herein to an "isomer" of zeaxanthin is used solely for convenience, to refer to a particular stereoisomer of zeaxanthin. Lutein is not regarded herein as an isomer of zeaxanthin.

Stereoisomeric differences in the various isomers of zeaxanthin which might appear small, subtle, and almost insignifcant are in fact extremely important, especially when it comes to retinal tissue. Apparently, the only zeaxanthin stereoisomer that is properly taken up and used by human retinal cells is the R-R stereoisomer.

There have been reports that trace quantities of the mixed "meso" isomer of zeaxanthin have been found in retinal tissue; however, these quantities are probably attributable to certain molecular conversions that can occur spontaneously within the retina, leading to formation of meso-zeaxanthin from lutein precursors (Bone, Landrum, et al, 1993 and 1994).

Carotenoid stereoisomers can be distinguished from each other using analytical methods such as chiral column chromatography (see, e.g., Bone, Landrum, et al, 1993) or circular dichroism analysis (see, e.g., Britton 1994).

Zeaxanthin and Lutein in the Macula (The Retinal Center)

As noted above, zeaxanthin and lutein are the two carotenoid pigments which give the macula (the yellow circle in the center of the retina) its characteristic yellow color. This section contains a chronology of the research efforts and discoveries that led to the current understanding of the presence and roles of zeaxanthin and lutein in the macula.

Wald 1949 was the first published article which identified lutein as one of the yellow pigments in animal retinas. In this work, nearly fifty years ago, Wald used spectrophotometry to analyze retinal extracts. The data he gathered indicated that one of the yellow pigments in retinal tissue had the same wavelength absorption pattern as lutein, which had already been identified and was known to exist in plants.

By 1970, the roles of carotenoids in protecting plants against light damage ("phototoxic" damage) had been well-established. It was also known by 1970 that various carotenoids were also present in animal tissue, and that all carotenoids in animal tissues were originally derived from plant sources, since animal cells and enzymes cannot synthesize carotenoids de novo. Building on those pieces of information, articles such as Foote et al 1970a and 1970b pointed out a number of functional similarities between carotenoids in animal and plant cells, and concluded that carotenoids protect against photodynamic damage not just in plants, but in animals also.

After the photo-protective role of carotenoids in animals was recognized, researchers began studying the chemistry and roles of carotenoids in the retina. One line of experiments involved tests in which lab animals were fed diets that did not contain any carotenoids; any plant-derived food they received was processed to remove any carotenoids, or it was made from grains or seeds that do not contain carotenoids (such as milo seeds). The results, reported in articles such as Malinow et al 1980, Kirschfeld 1982, Ham et al 1984, and Snodderly et al 1984, indicated that the retinas in carotenoid-deprived lab animals lost any yellow pigment in their macular areas, and that these retinas developed abnormally high quantities of soft drusen, which indicates damage to the retina, as described earlier. In view of these findings, researchers began suggesting that carotenoids appeared to be essential to healthy functioning of retinas. These researchers were, in effect, gathering molecular biochemical support for the age-old wisdom that carrots and leafy green vegetables contain things that are good for the eyes.

However, these findings did not pin down the chemical compositions of the retinal carotenoids, and they did not clearly establish the origin of the yellow pigments that define the macular region of the retina. Scientists did not yet know whether the yellow pigments in the retina had to be directly ingested in their final form, or whether they could be synthesized in animal cells from other carotenoid precursors, such as beta-carotene or lycopene.

In 1985, Bone et al reported that zeaxanthin was the other main carotenoid pigment in the macula. In 1986, a long review article by Handelman and Dratz (entitled, "The role of antioxidants in the retina and retinal pigment epithelium and the nature of prooxidant-induced damage") provided an extensive review of what was known about retinal carotenoids by then. It explicitly listed lutein and zeaxanthin as the macular pigments, and it speculated that, "The pigment also filters out potentially phototoxic blue light from the macula . . . carotenoids may be superior to alpha-tocopherol as free-radical quenching antioxidants" (p. 18).

Other relevant articles from the late 1980's include Werner et al 1987 (entitled, "Aging and human macular pigment density"), Pease et al 1987 ("Optical density of human macular pigment"), Haegerstrom-Portnoy 1988 ("Short-wavelength-sensitive-cone sensitivity loss with aging: a protective role for macular pigment?"), and Handelman et al 1988 ("Carotenoids in the human macula and whole retina"). Among other things, these articles established that zeaxanthin (which is fully conjugated, and which therefore offers somewhat better protection than lutein against damage caused by light energy) is the predominant pigment in the fovea, the small region at the very center of the macula. The quantity of zeaxanthin gradually decreases, and the quantity of lutein increases as one travels concentrically away from the fovea, toward the outer edges of the macula, so that at the outer periphery of the macula, lutein is the dominant yellow pigment.

More recent articles that address various aspects of retinal aging and damage, and which focus specifically on carotenoids as protective agents in the retina, include Sperduto et al 1990 (entitled, "Do we have a nutritional treatment for age-related cataract or macular degeneration?"), Gerster 1991 (a review article entitled, "Antioxidant protection of the ageing macula"), Schalch 1992 (another review article, "Carotenoids in the retina—a review of their possible role in preventing or limiting damage caused by light and oxygen," and Seddon et al 1994 ("Dietary carotenoids, vitamins A, C, and E, and advanced age-related macular degeneration").

In summary, it has been known for more than 10 years that lutein and zeaxanthin are the two carotenoid pigments in the macula, and scientists have been speculating ever since lutein and zeaxanthin were discovered in the retina that these two pigments may protect the macula against phototoxic damage. However, despite the fact that these discoveries and suggestions were all made more than 10 years ago, no one has yet developed any type of drug, nutritional or dietary supplement, or other form of treatment which is known to be truly effective in significantly preventing or retarding (let alone reversing) the gradual progression of macular degeneration.

The previous sentence needs to be qualified somewhat, since β-carotene, vitamin A, and vitamin E are all known to have some level of beneficial effect in helping to protect retinal tissue (see, e.g., U.S. Pat. No. 5,310,764, Baranowitz et al 1994, and the two articles by the Eye Disease Case Control Study Group, cited below). These patents and articles have claimed or suggested that β-carotene, vitamin A, and vitamin E can have a detectable effect in preventing or reducing the damage associated with macular degeneration. While such claims may be true, due to the general anti-oxidant roles of carotenoids, vitamin A, and vitamin E, it is also sadly true that the benefits provided by β-carotene, vitamin A, and vitamin E in the retina are very limited, and they do not rise to the level of truly effective treatments. For all practical purposes, macular degeneration must be regarded as unpreventable, unstoppable, and irreversible, and any broad-spectrum anti-oxidants (such as β-carotene, vitamin A, and vitamin E) are merely palliative measures. Since nothing that was truly effective was available, they have been used (with very limited success) to try to slow down the relentless damage caused by macular degeneration.

As a matter of prior art, it should also be noted many health food stores sell carotenoid preparations that are labelled as being beneficial to the eyes and eyesight. That labelling claim on carotenoid mixtures may be valid and reasonable, since (as noted above) β-carotene and vitamin A are known to be useful and beneficial in the eyes as general anti-oxidants. However, even though at least one commercially available carotenoid mixture that is sold in health food stores (the "Beta-Carotene Formula Preparation," sold by General Nutrition Corporation) lists zeaxanthin as one of the carotenoids contained in their carotenoid mixtures, none of the commercially available carotenoid mixtures contains more than extremely small, trace quantities of zeaxanthin. The great majority of the carotenoids in the carotenoid mixtures that are sold in health food stores are other, non-zeaxanthin carotenoids (mainly β-carotene and vitamin A).

The current positions and publicly stated research goals of several government agencies and research consortia are also worth noting. The National Institutes of Health, acting through the National Eye Institute (NEI) and the National Advisory Eye Council, has issued two recent government publications which are directly relevant. These two reports are "Vision Research: A National Plan 1994–1998,1" *NIH Publication No.* 93-3186 (1994; see pages 55–65 in particular), written by the members of the National Advisory Eye Council, and "Age related eye disease study," *NIH Publication* 93-2910 (1993). Both publications, and the research projects they describe, focus on β-carotene rather than zeaxanthin as the compound which holds the greatest apparent promise for treating AMD. To the best of the Applicants' knowledge and belief after discussing the subject with officials of the NEI, neither the NEI nor any other organization affiliated with the National Institutes of Health is willing to fund, or has recently funded, any research on zeaxanthin as a potential treatment for AMD. Instead, the NIH and various other tax-funded organizations are allocating millions of dollars to carry out research on β-carotene and other anti-oxidants as the most promising candidate agent for treating or preventing AMD.

Another research group that deserves attention (and which contains various members who are employed as researchers at the NEI) is the Eye Disease Case Control Study Group. This group recently published two articles entitled, "Antioxidant status and neovascular age-related macular degeneration," *Arch. Ophthalmol.* 11: 104–109 (1993), and "Risk factors for neovascular age-related macular degeneration," *Arch. Ophthalmol.* 10: 1701–1708 (1992). As in the official NIH reports, neither of these articles teaches or suggests the use of zeaxanthin as a drug for treating AMD. To the best of the Applicants' knowledge and belief, this consortium also has declined or refused to fund any research into zeaxanthin as a possible agent for treating or preventing AMD.

It should also be noted that there is an enormous level of interest in other biological roles for carotenoids, especially in their apparent ability to help reduce cancer rates. Since Peto et al brought this set of questions to the forefront in a major article published 1981, thousands of articles have been published which correlate carotenoid intake with reduced cancer risk.

In another peripheral but potentially important aspect of carotenoid biochemistry, Jialal et al 1991 suggested that carotenoids may play a role in preventing cholesterol formation and reducing the amount of plaque deposits that are formed inside arteries in patients suffering from atherosclerosis (hardening of the arteries). Although the Applicants have not seen any such comments in print, they have been told by ophthalmology researchers that there is some speculation among experts in this area that drusen, the cell debris that appears in the Bruch's membrane immediately behind the retina, may be analogous in several respects to plaque deposits in arteries. This speculation is believed to be one of the reasons behind the strong interest among many eye researchers in β-carotene as a retinal protective agent.

There is an enormous body of scientific literature dealing with the biological activities of carotenoids, and there has been great interest in ways to synthesize a number of important carotenoids, including lutein and zeaxanthin. However, despite all the carotenoid studies and all the carotenoid synthesis efforts of the past two decades, no one has yet reported any effective method of treating or preventing macular degeneration (except possibly for the use of β-carotene, vitamin A, and vitamin E as general antioxidants that might offer some limited palliative help).

In view of the enormous amount of damage and personal suffering that is inflicted on society and on victims of macular degeneration, that is a huge shortcoming. Accordingly, the subject invention offers a potentially very important breakthrough in providing both (1) a safe and effective drug for treating patients who have been diagnosed as suffering from macular degeneration, and (2) a nutritional supplement, comparable to a vitamin pill, which can and perhaps should be taken by anyone who wants to reduce the risk that he or she may eventually suffer from age-related macular degeneration after reaching middle age, or from any other form of macular degeneration at any age.

Synthesis of Lutein and Zeaxanthin: Prior Art

A number of articles and patents have described various methods for creating zeaxanthin. These prior art items can be grouped into two categories: fermentation methods, in which microbes play a key role in the manufacturing process; and non-fermentation synthesis methods, in which classical (non-microbial) chemical reactions are used. Most items of prior art in either class suggested that the zeaxanthin produced by those methods should be used for known purposes, such as poultry feed. However, it appears that none of those efforts ever resulted in actual production or sale of zeaxanthin in commercial quantities.

As of October 1995, the only way to purchase zeaxanthin, either in purified form, or in a semi-concentrated form in which zeaxanthin comprises more than about 5% of the weight of the preparation, requires the purchase of very small quantities of zeaxanthin (measured in milligram quantities) from specialty chemical manufacturers such as Atomergic Chemicals Corporation (Farmingdale, N.Y.) or Spectrum Chemical Manufacturing Company (Gardena, Calif.). The 1995 prices of purified zeaxanthin from these specialty manufacturers, in synthetic racemic mixtures that contain the undesired S-S and S-R isomers, ranges from about $90 to about $125 per milligram (which translates to about $100,000 per gram of zeaxanthin in a racemic mixture). Clearly, zeaxanthin is not a widely available chemical, and is not available to the public except in extremely small trace quantities, in mixtures of other carotenoids.

Prior art items which describe zeaxanthin production using microbial fermentation include the following:

(1) Courington and Goodwin 1955, which is the earliest known reference describing the production of zeaxanthin by microbes. The bacteria they described reportedly belonged in the genus Flavobacterium; however, as noted below, microbial classification definitions have changed a great deal over the past few decades, and those bacteria probably would not be classified as Flavobacterium under the current nomenclature.

(2) U.S. Pat. No. 3,891,504 (Schocher and Wiss, 1975, assigned to Hoffman LaRoche). This patent described the production of zeaxanthin by microbes from the genus Flavobacter, which were deposited with the American Type Culture Collection and given ATCC numbers 21081 and 21588. As with the Courington and Goodwin 1955 microbes, these microbes would not be classified as Flavobacter today. These cells and their zeaxanthin pigment were fed to chickens, and caused suitable coloration.

(3) U.S. Pat. No. 3,841,967 (Dasek et al, 1974, assigned to Nestle). This patent described the production of zeaxanthin by microbes from the genus Flavobacter; some of their work involved the same strain cited in the Hoffman-LaRoche '504 patent (21081 and 21588), and they also used ATCC strain 11947. This patent, as well as U.S. Pat. No. 3,951,743 (Shepherd et al, 1976, also assigned to Nestle) described certain cell culturing conditions and nutrient media that could be used to increase the quantity of zeaxanthin produced by the cells being cultured.

(4) Two more recent US patents (U.S. Pat. Nos. 5,308,759 and 5,427,783, both invented by Gierhart and assigned to Applied Food Biotechnology, Inc., the same assignee in this current application) describe a strain of bacteria (*Flavobacterium multivorum*) isolated from a Missouri waterway. These bacteria were discovered to create zeaxanthin without creating substantial quantities of other carotenoids. This is important, because it makes more zeaxanthin available as a pigment, when fed to poultry or fish to give their flesh a darker color. AFB's wild-type strain of *F. multivorum* was deposited with the ATCC, and was given ATCC accession number 55238. Because these bacteria generate a certain type of lipid called sphingolipids, the ATCC has provisionally reclassified these bacteria as *Sphingobacterium multivorum*, which is the name they are listed under in the ATCC's catalog. However, as of the filing date of this application, the Sphingobacterium name that appears in the ATCC catalog has not yet appeared in either of the reference works which are widely recognized as the official guides to microbial taxonomy: *Bergy's Manual of Systematic Bacteriology*, which is appended and updated by the International Journal of Systematic Bacteriology.

Gierhart's '759 patent claims methods for producing zeaxanthin, using AFB's *F. multivorum* bacteria. The '783 patent, which was a divisional, claims feed mixtures that can be given to poultry or fish. Both of these patents are limited to using zeaxanthin in poultry or fish feed; as noted above, although zeaxanthin is much more expensive than lutein, it is several times more effective (on a per-weight basis) than lutein in imparting color to animal flesh or chicken yolks. Neither of those patents says or suggests anything about using zeaxanthin for treating humans.

Various efforts to synthesize zeaxanthin by standard chemical means (without using microbial fermentation) have been reported over the past 20 years (e.g., U.S. Pat. No. 4,153,615, Saucy 1979). However, non-fermentation processes suffer from several disadvantages. They typically require numerous reaction steps, and each step has a less-than-100% yield, so that the final yield of zeaxanthin at the end of the multi-step processing tends to be relatively poor. In addition, chemical synthesis tends to yield undesired S-S and S-R stereoisomers of zeaxanthin, as well as various conversion products such as oxidized zeaxanthin, and zeaxanthin molecules which have lost one or more of the double bonds in the straight portion or end rings.

Recently, Hoffman-LaRoche obtained two US patents which relate to the chemical synthesis of the R-R isomer of zeaxanthin; these are U.S. Pat. Nos. 4,952,716 (Lukac et al 1990) and 5,227,507 (Lukac et al 1993). These processes require the production and purification of three major intermediates, with yields of approximately 70 to 85% for each intermediate from its precursor. The overall process described in the Lukac et al patents apparently requires a series of 14 reaction steps, which take a minimum of 83 hours (excluding purification), and the synthesis reactions yield a mixture of reactants and products. This reaction mixture must then be extensively treated to purify the R-R isomer of zeaxanthin. Accordingly, the entire process that would be required for both synthesis and purification using this technique would make production on a commercial scale very difficult, and extremely expensive.

Two types of poultry feed additives may be of interest, since they have the highest lutein or zeaxanthin quantities of any commercially available animal feeds. Certain types of poultry feed additives prepared from corn gluten contain a relatively high percentage of zeaxanthin (about 15–30%), when measured as a percentage of total carotenoids. However, the total carotenoid content of these feed additives is very low (only about 100 milligrams of total carotenoids per pound of poultry feed). The other type of poultry feed additive is prepared from marigold extracts. This additive contains roughly 100–200 times as much yellow pigment per pound of additive (i.e., about 10 to 20 grams of lutein and zeaxanthin per pound); however, more than 95% of the yellow pigment in this marigold preparation is lutein, not zeaxanthin. Zeaxanthin comprises only about 2 to 5% of the yellow pigment in this poultry feed additive (Bauernfeind 1981).

Any other animal feed additives that contain zeaxanthin contain it solely as a byproduct or trace ingredient, while other carotenoids are present in much higher quantities. Similarly, there is no source of zeaxanthin as a purified carotenoid for human use, either as a drug for patients suffering from macular degeneration, or as a vitamin or nutritional supplement.

Stereoisomerically Pure R-R Zeaxanthin Preparations

Neither of the US patents issued to Gierhart ('759 and '783) make any statements about any specific stereoisomers of zeaxanthin, since the status of the zeaxanthin stereoisomers generated by AFB's *F. multivorum* cells was not understood or appreciated in 1989, when the Gierhart applications were filed. This was especially true since both of these patents were solely concerned with creating zeaxanthin for use as animal feeds, to give poultry and fish a darker color.

By contrast, as noted above, different stereoisomers of zeaxanthin make an extremely important difference when zeaxanthin is being administered to humans as a drug for patients suffering from macular degeneration, or as a vitamin supplement for people who wish to take it as a preventive agent to reduce the risk of macular degeneration. The only zeaxanthin stereoisomer that is properly taken up by human retinal cells is the R-R isomer.

It has recently been discovered, using chiral column chromatography analysis (described in Bone, Landrum, et al, 1993) that AFB's *F. multivorum* strain (ATCC accession number 55238) and its mutagenized descendants generate the R-R stereoisomer as a sole isomer of zeaxanthin, or as a heavily dominant isomer (defined herein to refer to a mixture of carotenoid stereoisomers having at least 90% or more of a single stereoisomer). As described in detail in Example 4, an analysis by Prof. Landrum indicated that there are no detectable quantities of either the 3S-3'S isomer or the R-S meso isomer of zeaxanthin in the zeaxanthin preparations generated by fermenting AFB's *F. multivorum* strain (ATCC 55238).

This trait of stereoisomeric purity renders the zeaxanthin preparations made by fermenting this *F. multivorum* strain exceptionally well-suited for consumption by humans, either as a prescription drug for treating or retarding the progression of AMD damage in diagnosed victims, or as an over-the-counter vitamin or nutritional supplement for reducing the threat of AMD damage later in life, among people at risk.

This trait of stereoisomeric purity is extremely valuable, since it is extraordinarily difficult and expensive to separate different stereoisomers from each other. Although the separation of stereoisomers generated by chemical synthesis techniques may be possible in certain types of small-scale laboratory settings, it is prohibitively expensive, and effectively impossible, in large-scale commercial settings and volumes.

Accordingly, one object of this invention is to disclose that AFB's strain of *F. multivorum* (ATCC accession number 55238) and its mutagenized descendants generate the R-R stereoisomer of zeaxanthin as a sole detectable isomer, with no detectable quantities of the other undesired S-S or S-R stereoisomers.

Another object of this invention is to disclose the use of zeaxanthin produced by AFE's *F. multivorum* strain (ATCC accession number 55238) as a prescription drug to treat patients who have been diagnosed as suffering from macular degeneration, particularly age-related macular degeneration.

Another object of this invention is to disclose the use of zeaxanthin produced by AFB's *F. multivorum* strain (ATCC accession number 55238) as a nutritional supplement, in forms comparable to vitamin pills or as an additive in foods such as margarine, for reducing the threat of macular degeneration later in life.

Another object of this invention is to disclose that a preparation of zeaxanthin containing the R-R stereoisomer as the sole or heavily dominant isomer, and preferably also not containing other competing carotenoids which might reduce alimentary uptake or retinal deposition of zeaxanthin after ingestion, is a preferred composition for treating or preventing progressive retinal degeneration in humans.

These and other objects will become more apparent in the following summary and description of the invention.

SUMMARY OF THE INVENTION

This invention discloses a method of treating or preventing macular degeneration, one of the leading causes of blindness and vision loss, by administering a preparation of zeaxanthin which contains the 3R-3'R stereoisomer (also referred to as the R-R isomer, for convenience) as a sole or heavily dominant stereoisomer. Zeaxanthin, a yellowish pigment which is naturally present in macular cells in the center of the human retina, absorbs blue and near-ultraviolet light radiation, thereby protecting macular cells against phototoxic damage. The purified R-R isomer of zeaxanthin can be taken orally as a prescription drug by patients suffering from macular degeneration, and it can also be used as a nutritional supplement, in forms such as vitamin pills or food additives, by anyone who wants to reduce his or her risk of macular degeneration, which is widespread among people over the age of about 50 or 60. Zeaxanthin preparations which contain only the desired R-R isomer are produced by a strain of *Flavobacterium multivorum* cells (ATCC accession number 55238). These bacterial cells do not create any detectable quantities of the undesired S-S or S-R stereoisomers of zeaxanthin, and they do not synthesize significant quantities of other carotenoids such as β-carotene or lutein, which might compete against zeaxanthin for alimentary uptake after oral ingestion.

BRIEF DESCRIPTION OF THE DRAWINGS

FIG. 1 depicts the molecular structures of betacarotene, lutein, and zeaxanthin, showing the conjugated structure of all three carotenoids and the numbering system for the end rings. These molecular structures are known in the prior art.

FIG. 2 comprises a flow chart which describes the primary steps in fermenting and purifying zeaxanthin generated by microbes that synthesize stereoisomerically pure 3R-3'R zeaxanthin.

DESCRIPTION OF THE PREFERRED EMBODIMENTS

This invention discloses a method of using a zeaxanthin preparation to prevent, reduce, or otherwise treat a condition called macular degeneration, which causes eyesight loss in humans. To be suitable for human use, these zeaxanthin preparations must contain the 3R-3'R stereoisomer of zeaxanthin (also called the R-R isomer, for convenience) as a heavily dominant stereoisomer, and preferably should contain the R-R isomer as a sole detectable isomer, with no substantial and preferably no detectable levels of the undesired S-S or S-R stereoisomers.

In one preferred embodiment, an R-R zeaxanthin preparation as disclosed herein can be formulated and administered as a prescription drug, which will be prescribed by physicians to treat patients who have been diagnosed as suffering from macular degeneration, or to treat patients who have been diagnosed as having a specific genetic susceptibility to macular degeneration (such as a family history or genetic diagnosis of Stargardt's disease, Best's disease, Batten's disease, Sjogren-Larsson syndrome, cone-rod dystrophy, ovine ceroid lipofuscinosis, or a lysosomal storage disease such as Tay-Sach's disease).

To be effective as a prescription drug for patients suffering from macular degeneration, a zeaxanthin preparation as described herein must have a sufficient amount of the R-R isomer of zeaxanthin to rise to the level of a therapeutic agent. To achieve this level of therapeutic benefit, the zeaxanthin preparation must contain more than merely trace quantities of zeaxanthin, which are present in various mixed-carotenoid powders sold in health food stores. Formulations in capsule, tablet, or powdered form intended for use as a prescription drug should contain the R-R isomer of zeaxanthin at a concentration of at least about 2 percent, by weight. Expressed as absolute weight rather than a percentage, preparations intended for use as a therapeutic drug in patients suffering from macular degeneration preferably should contain at least about 3 milligrams of the R-R isomer of zeaxanthin, per dosage. Ingestible capsules containing up to about 25 milligrams (or any lesser quantity) can be created in a highly economical manner, using a single-step solvent extraction as described below. Capsules or powders containing higher quantities (such as 100 milligrams or more) can be created using more extensive zeaxanthin purification methods, such as the methods described in Example 4.

In an alternate preferred embodiment, the zeaxanthin preparation can be in the form of a vitamin or nutritional supplement, or food additive, to be consumed by people who do not currently suffer from macular degeneration, but who want to reduce their risk of macular degeneration later in life. When ingested for such purposes, appropriate dosages must be substantially higher than the trace quantities found in powders that are sold in health food stores today, but they will be substantially lower than when zeaxanthin is used as a therapeutic drug. Although preferred dosages for use as vitamin or nutrition supplements or food additives will need to be determined through human clinical studies, it is anticipated that such dosages are likely to be in the range of about 0.5 to 25 milligrams for a dosage to be ingested on a daily basis.

Regardless of whether it is used as a therapeutic drug or nutritional supplement, a zeaxanthin preparation intended for human use should contain the R-R isomer as a sole or "heavily dominant" stereoisomer. The term "heavily dominant stereoisomer" is used herein to describe a zeaxanthin preparation in which the desired R-R isomer constitutes at least about 90 percent of all zeaxanthin isomers in the mixture, so that any undesired S-S or S-R isomers constitute less than about 10 percent of all zeaxanthin in the mixture. Preferably, the R-R isomer should be the only detectable isomer, instead of merely a heavily dominant isomer. In actual practice, the bacterial fermentation described below generates the R-R isomer, not just as a heavily dominant isomer, but as a sole detectable isomer of zeaxanthin. If any other stereoisomers are present in the mixture after purification, their quantities are too small to be detected by the methods described in Example 4.

This invention also discloses a method of creating zeaxanthin preparations that contain the R-R isomer of zeaxanthin as a heavily dominant (or sole detectable) carotenoid. Unlike most bacterial strains, the *F. multivorum* cells described herein do not generate a substantial mixture of carotenoids; instead, this bacterial strain generates the R-R isomer of zeaxanthin as a sole detectable zeaxanthin isomer. Since zeaxanthin must compete against other carotenoids (including dietary carotenoids) for alimentary uptake and tissue deposition, this is highly useful for increasing zeaxanthin uptake and retinal deposition after oral administration, especially when zeaxanthin is being used as a drug to treat diagnosed cases of macular degeneration.

A preferred method of synthesizing isomerically pure R-R zeaxanthin involves fermentation of bacterial cells descended from a strain of *F. multivorum* which was deposited with the American Type Culture Collection and given ATCC accession number 55238. This strain of yellowish-orange pigmented bacteria was discovered and isolated by one of the Applicants (Gierhart) from a Missouri waterway. It does not synthesize substantial quantities of any other carotenoids, and it does not synthesize substantial quantities of undesired 3S-3'S or 3S-3'R stereoisomers of zeaxanthin; these discoveries concerning carotenoid and isomeric purity, were not described in either of the US patents (U.S. Pat. No. 5,308,759 and U.S. Pat. No. 5,427,783) that were issued previously to Gierhart and Applied Food Biotechnology.

As disclosed in U.S. Pat. Nos. 5,308,759 and 5,427,783, various steps can be used to create mutant strains that generate higher quantities of zeaxanthin. Such steps can use either randomly-acting mutagenic agents, or controlled genetic engineering techniques, followed by screening procedures which identify mutants or genetically-engineered offspring that generate higher quantities of zeaxanthin. Such screening procedures can be facilitated by using various known drugs (such as diphenylamine, nicotine, chlorophenylthiotriethylammonium hydrochloride, or lovastatin) which reduce the production of zeaxanthin by suppressing one or more enzymes involved in the metabolic pathways that generate carotenoids in plant or bacterial cells. When used at appropriate concentrations in screening tests, carotenoid-suppressing drugs such as these can be used to create hurdles that can be overcome only by mutant or genetically engineered offspring cells which produce abnormally high quantities of zeaxanthin, when compared to a parent strain.

Commercial-Scale Manufacture by Bacterial Fermentation

The following sections describe various steps that can be used to manufacture and purify commercial-scale quantities of isomerically pure R-R zeaxanthin.

As is well-known to those skilled in the art, many nutrients and methods that can be used to culture bacteria in small-scale lab tests become unduly expensive and difficult to monitor and control when an effort is made to convert them into large-scale commercial fermentation operations. Accordingly, the Applicants have invested substantial time and expertise in developing and testing nutrients and culture conditions for use with its *Flavobacterium multivorum* strains. The results of its research have generated preferred fermentation media and methods that are easier to work with and less expensive (per gram of zeaxanthin product) than the small-scale fermentation media and conditions disclosed in U.S. Pat. Nos. 5,308,759 and 5,427,783. The nutrient ingredients and reaction parameters that are currently preferred for commercial-scale fermentation are listed in Example 1, below.

The zeaxanthin produced by this type of bacterial fermentation needs to be stabilized in order to facilitate purification and preparation in stable formulations that have good shelf life. Stabilizing compounds can be added to the *F. multivorum* cells (or to a cellular extract containing zeaxanthin) at any time during a preparation or purification process; in general, one or more initial stabilizers should be added to the cells while they are still in a fermentation vessel, before pasteurizing or any other processing steps begin. Various candidate stabilizers have been tested by the Applicants, and the best results obtained to date use a combination of antioxidants listed in Example 2.

After the stabilizing compounds are added, a bacterial cell culture can be pasteurized by heating to 55° C. for 25 minutes. This kills the bacterial cells without damaging the zeaxanthin they have produced. The culture is then cooled to room temperature, and the zeaxanthin-containing cells and other solids present in the culture broth are separated from the liquid phase by mechanical means, such as cross-flow microfiltration, which can increase the cells/solids concentration from an initial value of about 10% to a filtered concentration of about 60 to 80% by volume. This procedure creates a cell paste, which also contains some residual solids from the nutrient medium.

Although this option has not yet been fully evaluated, it is possible that the *Flavobacterium multivorum* cells themselves, in intact form and possibly even in a viable state, may be suitable for direct ingestion by humans. A substantial number of human foods (including cheese, yogurt, beer, etc.) contain viable or killed-but-intact microbial cells, and there is no known pathogenicity associated with the *F. multivorum* cells isolated by Applied Food Biotechnology, Inc. They were isolated from a relatively cold artesian waterway, and since they are adapted to living in cold water, they cannot survive or reproduce well at temperatures inside the human body. In addition, these cells do not have any known toxic constituents; they are gram-negative, and do not have the cell wall structures that characterize gram-positive bacteria. When fed directly in the form of a cell paste to animals such as birds or fish, these cells appear to be well-suited as delivery vehicles for zeaxanthin. The zeaxanthin is released when the cells are digested by the animals, and the zeaxanthin is absorbed into the bloodstream and deposited into various tissues at expected and appropriate tissue locations.

Accordingly, intact *F. multivorum* cells containing the R-R stereoisomer of zeaxanthin may be suitable for direct human consumption, if desired, in any of three forms: (1) intact viable form; (2) intact killed form, after pasteurization or other suitable treatment; or (3) a formulation in which the bacterial cells have been killed and their membranes disrupted, to break open the cells and render the zeaxanthin more accessible, but in which the cells have not been treated to purify the zeaxanthin.

If desired, any cell preparation procedure disclosed herein can include a cell rinsing procedure, in which the nutrient medium and metabolites that remain after fermentation is complete is displaced and removed by flushing the cells with a solution containing any desired ingredients, such as stabilizers, preservatives, flavoring agents, etc.

Purification

After a cell paste has been created as described above, it can be treated in any of a variety of ways. If desired, the cell membranes can be disrupted, to break open the cells and render the zeaxanthin more accessible, by means such as sonication (high-frequency sound waves), high pressure, or grinding. Alternately, this step can be skipped if a solvent extraction procedure is used that disrupts the cell membranes.

If desired, a cell paste (with either intact or disrupted cells) can be dried to further concentrate the cells and increase the zeaxanthin fraction in the dried mass. This can be done by mechanical means such as spray drying (using heat) or lyophilization (freeze-drying under a vacuum). If drying is used, the resulting solid residue is usually referred to as a dried biomass; it usually contains about 1 to 10% zeaxanthin by weight, along with other cell solids, residual solids from the fermentation medium, and the stabilizers described above.

Either before or after (or in lieu of) the disruption or drying steps, an extraction step can be carried out to concentrate the zeaxanthin, which accumulates mainly in the cell membranes. Suitable solvents for extraction generally include polar organic solvents. The best solvent identified to date (i.e., the solvent which provides both the ability to extract zeaxanthin away from the bacterial membranes, and which provides a high solubility level for zeaxanthin) is tetrahydrofuran (THF), a five-member ring with an oxygen atom at one corner. This solvent aggressively attacks the cell membranes, and renders a separate disruption step unnecessary. Although stirring is not necesary when THF is used in lab-scale operations, stirring during the solvent mixing step would probably be beneficial in commercial-scale operations.

Other solvents have also been tested and will continue to be tested and evaluated for zeaxanthin extraction and solubility, even though none tested to date work as well as THF. As mentioned above, the polar organic solvents appear to offer the best class of solvents for this type of use. Non-ringed organic solvents tested to date (such as acetone and diethyl ether) have somewhat lower solubility levels, while solvents such as methanol, ethanol, and hexane have even lower zeaxanthin solubility levels.

In general, solvent extraction involves mixing a solvent with the cell paste or dried biomass, under conditions that cause the solvent to dissolve as much of the zeaxanthin as possible. This step is followed by separating the solvent-soluble liquid fraction from the solids, using mechanical means such as centrifugation or filtering. The solids that remain after separation can be discarded, or used as feedstock for other processing steps (including repeated solvent extraction cycles, if desired). The solvent-soluble liquid fraction is then treated to remove the solvent, usually by evaopration at a suitable temperature and pressure. This leaves behind a viscous oil which contains the solvent-extracted zeaxanthin along with other solvent-soluble components that were drawn out of the cell paste by the solvent. When THF was used as the solvent in a single-pass extraction process on cells containing from 1 to 3% zeaxanthin by weight, the zeaxanthin content in the extracted oily material was increased to about 5% to about 20%, by weight.

Another type of solvent extraction which has been evaluated in preliminary tests with good results involves the use of a super-critical liquid (i.e., a compound which is normally a gas at atmospheric pressures, but which becomes a liquid which acts as a solvent at elevated pressure). Carbon dioxide is the most widely used solvent in supercritical extraction, and commercial-scale $CO_2$ extraction systems which operate at pressures of 5,000 psi or higher are available from various suppliers. In such systems, liquified carbon dioxide is mixed with a cell paste or dried biomass inside a high-pressure reaction vessel, and the liquid is then passed through a series of subsequent chambers that reduce the pressure in a step-wise manner. Zeaxanthin precipitates out of the solution at a fairly high pressure, while a large number of other cell solids remain dissolved in the supercritical liquid. The zeaxanthin precipitate can therefore be collected during an early de-pressurizing step, while the large majority of impurities remain soluble in the carbon dioxide and will be carried away in the solvent to other reaction chambers where the pressure is reduced further. The efficiency of supercritical solvent extraction can be further increased by using entraining agents (such as ethanol, propylene glycol, or ethyl acetate). Several of these entraining agents have been preliminarily tested, and have been shown to substantially increase the solubility of zeaxanthin in supercritical carbon dioxide.

Although carbon dioxide is the most widely used supercritical agent, various other compounds (including various nitrogen or chlorofluorocarbon compounds) are also used for similar purposes in commercial-scale systems. Any such compound which goes through both gaseous and liquid phases as a function of pressure can be tested for suitability for purifying zeaxanthin by supercritical extraction after a fermentation process.

If desired, an oily zeaxanthin-containing fluid generated by solvent extraction as described above can be mixed with a lipophilic carrier substance (such as vegetable oil), and then enclosed within a capsule designed for direct human ingestion, without requiring any further purification of the zeaxanthin. This will provide a suitable and economical method of making a a semi-pure digestible form of the R-R isomer of zeaxanthin available for human use, either as a drug for people suffering from macular degeneration, or as a vitamin or nutritional supplement for people who want to reduce their risk of suffering macular degeneration later in life.

Alternately, a semi-pure form of R-R zeaxanthin (such as the oily fluid created by solvent extraction as described above) can be purified further, if desired, to increase the zeaxanthin concentration and remove any impurities. This can be done by any of several means, including (1) two-solvent systems which use a combination of two selected solvents; (2) crystallization or adsorption on a substrate (such as a woven filter bed) that encourages crystallization of zeaxanthin; or (3) other processing techniques, such as counter-current chromatography. A chromatography method which was used by the Applicants to purify the R-R isomer of zeaxanthin to about 98% purity is described in Example 4.

A different purification technique for lutein, a different carotenoid, is disclosed in U.S. Pat. No. 5,382,714 (Khachik 1995; also see Khachik et al 1991). This method, which uses ethanol and water in a two-solvent extraction system followed by lyophilization, may be well-suited to purifying zeaxanthin produced as described above to a purity level of 90% or higher, in commercial quantities. Another potentially relevant patent is U.S. Pat. No. 4,851,339 (Hills 1989), which describes purification of carotenoids from algae.

Since the quantities of unwanted carotenoids generated by AFB's *F. multivorum* strain (ATCC 55238) are very low, any purification technique which has been developed for lutein (or any other carotenoid compound) can be tested on a zeaxanthin preparation created by this *F. multivorum* strain. Due to various chemical similarities between β-carotene, lutein, and zeaxanthin, any such purification method which works satisfactorily on β-carotene or lutein is very likely to give good results in purifying zeaxanthin as well. The suitability of any known purification technique, developed for any carotenoid, can be evaluated for zeaxanthin using no more than routine experimentation.

Modes of Administration to Humans

This current patent application is being filed simultaneously with a related application that describes and claims various formulations intended for oral ingestion by humans. That related application describes a number of preferred modes of packaging zeaxanthin for human ingestion, including the following: (1) an oily fluid containing zeaxanthin, generated by a simple and economical solvent extraction step, can be mixed with a lipophilic carrier liquid such as vegetable oil and enclosed within a digestible capsule; (2) an oily fluid containing zeaxanthin can also be added to margarine, syrup, cookie dough, meat products that will not be subjected to harsh cooking, or any other suitable food product, and can be ingested as part of those foods; (3) a granular or powdered form of zeaxanthin, which can be generated by additional processing of the oily fluid, can be used as a soup or salad enhancement, as a component in an herbal or spice mixture, or in other such formulations; and (4) an oily fluid or granular formulation can be added to other vitamins, to form a multi-vitamin tablet, capsule, or powder. Any of these formulations can be used to enhance stability and availability and promote the use of isomerically pure R-R zeaxanthin. That related patent application, entitled, "Zeaxanthin Formulations for Human Ingestion," has been given Ser. No. 08/551,153 by the U.S. Patent and Trademark Office. The contents of that related application are incorporated herein by reference; upon issuance of a US patent based upon this current application, the contents of that related application will be opened for public inspection, if not already issued as a US patent.

Periodic oral ingestion is the preferred mode of administering zeaxanthin for retinal protection purposes, using ingestion modes such as daily or weekly capsules, or occasional use of zeaxanthin-supplemented food preparations such as margarine. "Periodic" ingestion does not require regular ingestion at fixed intervals (such as daily or weekly pills), but instead refers to occasional, intermittent ingestion which allows a reasonable period of time (such as several days) to elapse between dosages, thereby allowing appropriate and gradual deposition of small quantities of zeaxanthin in the macular tissue. As with any vitamin supplement, a single dosage may be beneficial, but a single dosage will not be as beneficial over a period of years as periodic ingestion of appropriate small dosages. Pharmacodynamic studies on carotenoid uptake in humans and test animals suggest that daily ingestion is preferable to weekly or other sporadic intake, due to "loading" factors that are manifested in blood concentrations.

Since alimentary uptake of carotenoids tends to be relatively low, it may be medically desirable for certain patients (such as patients suffering from severe macular degeneration) to use other forms of administration, such as intramuscular or intravenous injection, or implantation of a slow-release device. If this route is chosen for a specific patient, it can be carried out using implantable devices or injectable carrier liquids known to those skilled in the art.

Carrier formulations that are used for injection of hydrophobic compounds typically include water, a buffering agent, and an organic compound having a plurality of hydroxyl groups, such as propylene glycol or dextran or cyclodextrin compounds. Any such carrier formulation can be tested for use in injecting zeaxanthin if desired, using routine experimentation.

As discussed in the Background section, various types of macular degeneration can be diagnosed by ophthalmologists, using specialized retinal photography to evaluate the quantity of soft drusen in or behind the retina. This diagnostic method can supplemented by other diagnostic techniques if desired, including in vivo lipofuscin analysis as described in Dorey et al 1993. Such tests are usually carried out by a specialist if an eyesight test by an optometrist indicates a significant loss of peripheral vision.

If a patient has been diagnosed as suffering from macular degeneration, then an ophthalmologist or other physician can prescribe administration of the R-R isomer of zeaxanthin to the patient, as a drug, to treat the condition. As noted above, the term "treat" is used broadly herein, to include any treatment which reduces, reverses, delays, prevents, or otherwise ameliorates the progressive damage caused by macular degeneration.

The "dry" form of age-related macular degeneration (i.e., the form of macular degeneration which appears most commonly in people over the age of 50, and which does not involve aggressive capillary growth into the retina) is of primary interest herein, since most cases of dry AMD are likely to involve an inadequate supply of zeaxanthin (a protective agent) in the macula as one of the etiological agents of this class of macular degeneration. Indeed, an inadequate supply of zeaxanthin as a protective agent, coupled with high levels of exposure to direct sunlight, may well be the two primary causes of AMD.

However, even though dry AMD is the primary type of AMD which is of principle interest herein, it is also recognzied and anticipated that the R-R isomer of zeaxanthin will also be prescribed and used (or at least tested) as a treatment for any and all other types of macular degeneration.

There are two major reasons why zeaxanthin will be prescribed and used as a potential treatment for other types of macular degeneration. First, with the exception of a broad claim that various anti-oxidants (mainly β-carotene, vitamins A, C, and E, and selenium) are generally beneficial to the eyes and eyesight, no other treatments are effective in stopping the advancing retinal damage caused by other forms of macular degeneration (including the wet form of macular degeneration caused by aggressive capillary growth into the retina). Even the best treatment currently known for fighting wet macular degeneration (i.e., laser ablation of the encroaching capillaries) is not a permanent cure, and can only stave off blindness for a limited period of time.

Since there are no other treatments which are truly effective for other types of macular degeneration, then any agent that can be used effectively to stop the encroaching damage caused by any type of macular degeneration will (and should) be carefully tested and evaluated. Zeaxanthin falls within the category of a highly promising treatment, and it should and will be tested to see whether it can help reduce, retard, or even reverse the damage caused by any and all forms of macular degeneration.

And second, zeaxanthin acts as a protective agent in the retina. It provides a mechanism for safely absorbing and handling excess light energy in the blue and near-UV range; in this manner, it protects retinal cells and photoreceptors against phototoxic damage. Even if an unrelated etiologic agent (such as aggressive capillary growth) is the immediate or initial cause of macular degeneration in a specific patient, any type of secondary damaging agent will cause even more damage in a system that is being subjected to high levels of stress and disruption. Accordingly, a simple treatment that can help restore or supplement the quantity of a protective agent inside a retina that is under attack is likely to help promote and enhance the retina's ability to sustain its natural and proper homeostasis and defend itself against the attack.

Accordingly, this invention discloses a method of increasing the concentration of a natural and beneficial protective agent in the retinas of patients diagnosed as suffering from macular degeneration, to help protect and defend the macula and to help it sustain its desired homeostasis, regardless of the specific etiologic agent which is causing the degeneration in a specific patient, and regardless of the particular type of macular degeneration which is occurring in the eyes of a specific patient.

Furthermore, as a protective agent, the R-R isomer of zeaxanthin can help provide a beneficial effect at any stage of macular degeneration, regardless of whether it is early-onset, moderate, or advanced macular degeneration, provided that total blindness has not yet occurred and some portion of the macula remains functional.

However, it is not claimed or expected that the R-R isomer of zeaxanthin described herein will "cure" macular degeneration. This treatment is not expected to reverse retinal damage that has already occurred, or to restore damaged retinal tissue to a pristine condition. Nevertheless, it offers a highly useful and benefical treatment for macular degeneration, in the form of a drug that can slow down and retard the encroachment of additional degeneration.

It is also recognized and anticipated by the Applicants that the isomerically pure R-R form of zeaxanthin can (and should) be used as a nutritional supplement, in formulations comparable to vitamin pills or as an additive in suitable foods such as margarine, which will be ingested by people who have not been diagnosed as suffering from AMD but who are concerned about protecting their eyesight over the long term. Dietary supplements containing the R-R isomer of zeaxanthin (in pills, powders, syrups, margarines, etc.) are likely to be widely recommended to the public by physicians and other health care professionals, and by government, educational, insurance, and other organizations interested in preventing blindness.

Testing Zeaxanthin in Animals

In in vivo tests, zeaxanthin that has been synthesized using *F. multivorum* cells descended from the ATCC 55238 strain is being tested for retinal protection in a selected bird species, *Coturnix coturnix japonica*, commonly called the Japanese quail. This species provides a useful animal model of macular degeneration in humans, due to a number of factors, including:

(1) The entire retina of the Japanese quail resembles the macular area of the human retina in a number of important anatomical and physiological aspects. For example, the quail retina contains both zeaxanthin and lutein, and it is rich in photoreceptor cones rather than rods.

(2) The Japanese quail retina displays some of the same manifestations of pathology as human retinas. For example, Japanese quail retinas accumulate soft drusen and lipofuscin, which are strongly correlated with onset of AMD in humans.

(3) Although quail retinas are much smaller than human retinas, the entire quail retina is colored yellow, due to the presence of zeaxanthin and lutein. This effectively allows the entire retina of a quail to serve as a model of the small macular region at the center of a human retina, and it renders analysis and observation much easier.

(4) The retina of the Japanese quail is avascular, and has a structure similar to the foveal region of the human retina.

(5) Japanese quail have a life-span of roughly 1 to 1.5 years for females, and 3 to 4 years for males. This allows "longitudinal" studies of aging processes which would be impossible in monkeys or humans.

These factors are discussed in more detail in Fite et al 1991 and Fite et al 1993.

These in vivo tests, which have been commenced but not yet completed as of the filing date of this application, are described in Examples 5 and 6.

Microbial Sources of R-R Zeaxanthin

The strain of *Flavobacterium multivorum* cells disclosed herein and deposited with the ATCC (ATCC accession number 55238; as noted above, these are referred to as *Sphingobacterium multivorum* in the ATCC catalog, but their name has not been changed in the Bergy's Manual) provide those skilled in the art with at least three distinct pathways to microbially synthesize isomerically pure R-R zeaxanthin.

First, direct and unmodified descendants of these cells can be used in fermentation reactions which synthesize the desired R-R isomer of zeaxanthin with essentially no detectable quantities of other undesired stereoisomers. The total carotenoids generated by these cells comprise more than 90% zeaxanthin, the desired carotenoid.

Second, descendants of the ATCC 55238 strain can be used after they have been modified in ways which increase their levels of production of the R-R isomer of zeaxanthin. Such mutants and other variants can be created by any of several methods that depend on random or semi-random events, followed by screening tests to identify colonies that have the desired trait of increased zeaxanthin production. Techniques which utilize random or semi-random events include (1) treating descendants of the wild-type ATCC 55238 strain with randomly-acting mutagenic agents, such as ultraviolet or X-ray radiation, or various known chemical mutagens, such as N-methyl-N'-nitro-N-nitrosoguanidine; (2) generating sexual combinations, by mixing the *F. multivorum* cells with other types of bacteria that actively promote conjugation and exchange of DNA between bacterial cells; or (3) treating the *F. multivorum* cells of this invention with bacterial transposons or viruses that can cause the rearrangement of relatively large chunks of DNA. These techniques (and various other specialized techniques known to those skilled in the art) effectively introduce uncontrollable and random alterations in each of thousands or millions of descendant cells with mutated or otherwise altered genetic content. Therefore, these techniques must be used in conjunction with cloning and screening techniques, to identify and isolate the small fraction of offspring which have the desired trait of increased zeaxanthin production. As mentioned above, these screening tests can be facilitated by using drugs (such as diphenylamine, nicotine, or lovastatin) which suppress one or more enzymes involved in the biosynthetic pathway that generates zeaxanthin. In layman's terms, these suppressor drugs create "hurdles" which can be overcome only by mutant cells that produce abnormally high quantities of zeaxanthin.

Fortunately, the analytical tests which can be used to identify high-producing mutant strains are, in most cases, remarkably simple, fast, and easy. Since zeaxanthin is a yellow pigment, simple visual observation of a culture plate can be used to identify mutant colonies which have the desired traits of (1) good cell growth rates, and (2) the ability to generate abnormally high quantities of the yellow pigment. If desired, automated equipment (such as 48-well or 96-well plate readers, or cell sorting devices coupled to flow cytometers) can also be used in screening tests after a mutagenic step.

All of these mutagenesis and screening techniques are conventional and well-known in this field of art. Regardless of the particular methods or reagents used to introduce random or semi-random events into mutagenized descendant cells, any cells which are directly descended from the ATCC 55238 strain are regarded as descendants of the wild-type ATCC 55238 cells, even if they have been modified or mutagenized in any of the ways listed above.

In the third alternate approach, non-descendant microbial cells can be created which contain genes which express enzymes that contribute to the synthesis of the desired R-R isomer of zeaxanthin, and which have been isolated or otherwise derived from the *F. multivorum* cells described herein (ATCC 55238). Such genes can be isolated and identified using known genetic engineering techniques, such as by using DNA sequences obtained from the carotenoid-producing "crt" gene sequences listed in U.S. Pat. No. 5,429,939 (Misawa et al 1995, discussed above) as hybridization probes to search for carotenoid-producing genes having homologous DNA sequences in the genome of *F. multivorum* (ATCC 55238). Carotenoid-producing genes which are isolated from *F. multivorum* (ATCC 55238) using this technique or other known techniques can be inserted into plasmids, cosmids, phages, or other suitable vectors that can be used to genetically transform any desired type of host cell, such as *E. coli* cells, yeast cells, insect cells, or mammalian cells. This type of controllable genetic engineering will allow genetically transformed cells to express zeaxanthin-producing genes obtained from *F. multivorum* cells (ATCC 55238).

In addition, the protein-encoding portions of the zeaxanthin-producing genes from *F. multivorum* (i.e., those portions of the genes which are transcribed into messenger RNA which is subsequently translated into enzymes or other peptides that are involved in the biosynthetic pathway that generates zeaxanthin) can be placed under the control of high-powered and/or inducible gene promoters. Such "chimeric" genes with enhanced gene promoters can be used for various purposes, such as (1) to suppress expression of zeaxanthin-producing enzymes during a cell growth phase, and then to greatly increase expression of the zeaxanthin-producing enzymes by the cells shortly before the zeaxanthin is extracted or the cells are harvested; and (2) to insert the genes into other types of host cells which have different characteristics that may be preferred for certain types of commercial production, such as *E. coli* cells or yeast cells, which are widely used cell types that can benefit from well-established and highly optimized fermentation, handling, and purification techniques.

Zeaxanthin-producing genes isolated from the *F. multivorum* strain described herein can also be enhanced by other genetic engineering techniques known to those skilled in the art. As one example, bacterial cells often use "non-preferred" codons in mRNA coding sequences, to regulate the quantity of a protein which is translated from mRNA molecules. To sidestep this natural limiting mechanism, non-preferred codons in an mRNA coding sequence of a zeaxanthin-producing gene isolated from *F. multivorum* can be replaced by "preferred" codons which will increase the expression of a zeaxanthin-producing enzyme in a selected type of host cell.

As another example, cysteine residues can hinder the activity or stability of an enzyme, by forming undesired disulfide bonds with other cysteine residues, either in the same or other protein molecules. Accordingly, the activity or stability of an enzyme can sometimes be increased by replacing one or more cysteine residues with less reactive amino acids (e.g., U.S. Pat. No. 4,737,462, by Mark). In addition, the expression of a protein can often be increased by substituting codons for common amino acids such as glycine, in place of codons that code for methionine and tryptophan, which are less common and which tend to slow down and reduce the expression of protein from mRNA molecules. After a synthetic gene is created which causes an amino acid substitution of this nature, the modified protein can be tested to determine whether it retains the desired enzymatic activity while being expressed in higher quantities or more stable form.

These are just a few examples of known genetic engineering techniques that can be tested and evaluated on zeaxanthin-producing genes isolated from the *F. multivorum* strain described herein, using no more than routine experimentation, to determine whether any such modification will enhance the production of zeaxanthin by a desired type of bacterial, yeast, or other host cell.

The phrase in the claims which refers to "cells which have been genetically engineered to contain at least one zeaxanthin-synthesis gene containing a DNA sequence obtained from a strain of *Flavobacterium multivorum* which has been given ATCC accession number 55238" includes cells containing genes having DNA sequences that were chemically synthesized, using a DNA or mRNA sequence determined by analyzing the ATCC 55238 cells or descendants thereof. In vitro DNA synthesis techniques are well known in the art, and can be used to duplicate a selected gene sequence from a certain type of cell without requiring direct replication of the cell. A "zeaxanthin-synthesis gene" includes any gene which expresses an enzyme or other protein that is involved in the zeaxanthin biosynthetic pathway, and which can be used to increase zeaxanthin production if inserted into suitable host cells, regardless of which particular zeaxanthin biosynthesis enzyme the gene encodes.

EXAMPLES

Example 1

Commercial-Scale Fermentation

The nutrient medium that was preferred by the Applicants for lab-scale testing of *Flavobacterium multivorum* was identified as nutrient medium E under Example 3 in U.S. Pat. Nos. 5,308,759 (Gierhart 1994) and 5,427,783 (Gierhart 1995). This lab-scale medium contained several ingredients that were expensive and difficult to work with, and substantial work to create a better commercial-scale nutrient medium was carried out after the initial filing date of those applications. The nutrient media that are currently preferred for commercial-scale fermentation have eliminated corn flour and several other ingredients, and contain either high maltose corn syrup or sugar beet molasses at concentrations ranging from 1 to 10% w/v, along with corn steep liquor at 0.5 to 4% w/v; ammonium sulfate heptahydrate at 0.5% w/v; sodium chloride at 0.5% w/v; magnesium sulfate heptahydrate at 0.1% w/v; sodium acetate at 0.1% w/v; ferrous sulfate heptahydrate at 0.001% w/v; yeast extract at 0.2% w/v; thiamine-HCl at 0.01% w/v; between 1 and 6% w/v hydrolyzed casein (such as NZ Amine HD, sold by Sheffield Products, Division of Quest International, Norwich, N.Y.); and vegetable oil at 1% v/v.

After these ingredients are mixed together, sufficient NaOH is added to raise the pH to 6.5; by contrast, when the nutrient medium was adjusted to pH 7.5, as described in the lab-scale experiments in U.S. Pat. Nos. 5,308,759 and 5,427,783, too many solids precipitated out from the corn steep liquor.

The culture medium is sterilized by autoclaving at 121° C. for 30 minutes, then it is cooled to 27° C. and inoculated with 5 to 10% v/v of a "liquid preculture" containing a strain of *F. multivorum* which produces the R-R isomer of zeaxanthin without producing S-S or S-R isomers of zeaxanthin, and without producing any other carotenoids in significant quantities.

The cells used to prepare a liquid preculture are maintained on a slant tube of plate count agar. These slant cultures are inoculated with clonal colonies of *F. multivorum* descended from the strain deposited by the Applicants with the ATCC, and given ATCC accession number 55238. After incubation for 48 hours at 28° C., stock slants are refrigerated at 4° C. until use as inoculum for liquid media. Viable cells can also be frozen using conventional freezers, dry ice, or liquid nitrogen, for prolonged storage.

A liquid preculture is prepared using cells taken from an agar slant to inoculate 30 mL of liquid media prepared as described above, contained in a 300 mL baffled flask. The growth conditions are 28° C. at pH 7.2 to 7.6, aerated by agitation at 250 RPM and cultivated for 24 hours. After an initial 24 hour incubation, the cells contained in one or more 30 mL preculture flasks are used to inoculate a ten-fold greater quantity of nutrient medium in a suitably sized fermentation vessel. The cells are then incubated for 48 to 72 hours at 28° C. The pH is maintained between 6.80 and 7.20 using NaOH and/or phosphoric acid. The dissolved oxygen level is kept at 30 to 40% of saturation by bubbling filtered air through the vessel at a rate of 1 volume of air per one volume of liquid per minute while agitating the vessel at 400 to 1000 RPM. Tests using periodic sampling and high performance liquid chromatography have indicated that maximum quantities of zeaxanthin will usually be produced within about 72 hours when the cells are fermented under these conditions.

Example 2

Addition of Stabilizing Agents

Zeaxanthin produced by the fermentation processes of Example 1 needs to be stabilized in order to facilitate subsequent purification and formulation, and to ensure purity. Stabilizing compounds can be added to the *F. multivorum* cells (or to a cellular extract containing zeaxanthin) at any time during a preparation or purification process; in general, one or more initial stabilizers should be added to the cells while they are still in the fermentation vessel.

Various candidate stabilizers have been tested by the Applicants. The best results obtained to date have used a combination of stabilizing agents, which are mixed together in a small quantity of a suitable solvent (such as about 2 milliliters of ethanol for a 20 liter fermentation vessel) before being added to the cells. The preferred stabilizer mixture contains tertiary butyl hydroquinone (abbreviated as TBHQ; also called 2-(1,1-dimethyl)-1,4-benzenediol) at a quantity which will generate a final concentration ranging from about 250 µg/L up to about 50 mg/L after being mixed with the cells; ethoxyquin at a post-mixing concentration ranging from about 250 µg/L to about 250 mg/L; α-tocopherol at a concentration ranging from about 250 µg/L to about 250 mg/L; and EDTA (ethylene diamine tetra acetic acid) at a concentration ranging from about 500 µg/L to about 500 mg/L. Suitable concentrations can vary widely, and will depend on various factors such as subsequent purification steps and the intended mode of packaging and ingestion. Preferred concentrations for single-pass THF extraction followed by mixing with vegetable oil and water-tight encapsulation in a vitamin-type pill are about 25 to 50 mg/L for TBHQ; 250 to 500 µg/L for ethoxyquin, 250 to 500 µg/L for α-tocopherol; and 500 to 1000 µg/L for EDTA.

After the stabilizing compounds are added, the cell culture is pasteurized by heating to 55° C. for 25 to 50 minutes. This kills the bacterial cells without damaging the zeaxanthin they have produced. The culture is then cooled to room temperature, and the zeaxanthin-containing cells and other solids present in the culture broth are separated from the liquid phase by means of a cross-flow microfiltration system which increases the cells/solids concentration from an initial value of about 10 to 15%, to a filtered concentration of about 60 to 80%, by volume. This procedure results in a cell paste, which also contains some residual solids from the nutrient medium.

For zeaxanthin preparations that are fed to Japanese quail for retinal testing, as described in Examples 5 and 6, the cell paste is frozen to −70° C., then dried by lyophilization at 25° C. at full vacuum, to create a dried biomass containing about 1 to 10% zeaxanthin by weight. In past tests, the quantity of zeaxanthin in each batch was individually measured, and batches having different concentrations were combined and mixed together to ensure consistent concentrations for the Japanese quail tests. To create zeaxanthin preparations for human ingestion, solvent extraction is used to generate a viscous oily fluid as described in Example 3.

Example 3

Semi-Purification into an Oily Liquid

After a cell paste has been created as described in Example 2, it can be treated in any of a variety of ways. As mentioned in the Description of the Preferred Embodiments, the cell membranes can be disrupted if desired, to break open the cells and render the zeaxanthin more accessible, by means such as sonication (high-frequency sound waves), high pressure, or grinding, keeping the temperature of the cells below about 30° C. to prevent oxidation. However, this step has not been necessary when tetrahydrofuran (THF) is used in a solvent extraction step, since THF is quite effective in disrupting the cell membranes without mechanical assistance. Stirring has not been necesary when THF is used in lab-scale operations; however it is likely that stirring during the solvent mixing step would probably be beneficial in commercial-scale operations.

In tests done to date, THF extraction involved mixing about 8 to 20 volumes of purified filtered THF with a volume of cell paste containing 60–80% solids, at a temperature below 25° C., for a period of 2 to 24 hours. The THF aggressively attacks the cells, creating a liquid fraction with what is, in essence, a suspension of flocculant solids in the liquid. The majority of the THF is removed by decanting, which can follow centrifugation at up to 20,000 gravities for several minutes. The THF that remains after decanting can be evaporated at room temperature under full vacuum, to leave behind a viscous oily mass which usually contains about 10% zeaxanthin by weight. Zeaxanthin content in the oily fluid has ranged from about 5 to about 20% zeaxanthin, when cell pastes containing 1 to 3% zeaxanthin are treated by THF extraction in a single-pass operation.

Example 4

Preparation of Highly Purified Zeaxanthin in Dry Powdered Form, with 100% Pure R-R Isomer A highly purified zeaxanthin preparation in dry powdered form was created by processing the THF-extracted oily fluid described in Example 3 by means of liquid chromatography, as follows. The oily ZX-containing liquid was dissolved in hexane, and then passed through a chromatography column containing neutral alumina powder. Two column-volumes of hexane were used to wash the column, to remove carotenoid impurities such as β-carotene and lycopene, as well as lipids and other contaminants. A mixture of hexane:acetone at 80:20 was then passed through the column, to release the zeaxanthin. The dissolved zeaxanthin which emerged was collected and dried under vacuum. Chromatographic analysis of the fresh preparation indicated that it was at least 98% pure zeaxanthin; only trace quantities of any impurities were detectable.

After roughly six months of storage in a relatively unprotected state (usually under normal refrigeration with moderately frequent removal; without containing any antioxidants, and without taking any precautions to prevent contact by atmospheric oxygen), a sample of the zeaxanthin preparation was sent for stereoisomeric analysis to Prof. John Landrum (co-author of the Bone, Landrum, et al papers) at Florida International University in Miami. His analysis, using chiral column chromatography with dicarbamate derivatization, indicated that the six-month-old unprotected preparation contained 92% zeaxanthin. The impurities appeared to be mainly keto-carotenoids which pre-eluted before the zeaxanthin; keto-carotenoids have an extra oxygen atom attached somewhere to a carotenoid, and they are common by-products that arise when carotenoids are stored without being protected against oxidation.

Prof. Landrum's chiral analysis indicated that 100% of the zeaxanthin in the preparation was the desired R-R isomer. There were no detectable quantities of the undesired S-S or S-R isomers of zeaxanthin.

It is recognized that chromatography purification as described above, although entirely feasible and highly effective, is not ideally suited to preparing highly purified zeaxanthin in commercial quantities. An alternate method that was developed to purify lutein, described in U.S. Pat. No. 5,382,714 (Khachik 1995; also see Khachik et al 1991), which uses a cold ethanol-water mixture in a two-solvent extraction system, followed by lyophilization, offers a good candidate for evaluation for commercial preparation.

Example 5

Tests of Zeaxanthin on Japanese Quail, Using Different Dietary Groups

All tests involving Japanese quail are being carried out at the Schepens Eye Research Institute of Harvard Medical School (Boston, Mass.), under a contract with Applied Food Biotechnology, Inc. All treatment or control groups contain statistically significant numbers of birds. In most cases, control population groups are the same size as treatment population groups.

All carotenoid-deficient bird feeds are obtained from Purina Mills (St. Louis, Mo.). These bird feeds are sold for experimental use only, and are obtained by using grain (such as milo seeds) that is naturally devoid of carotenoids.

All zeaxanthin preparations which are fed to the Japanese quail are in the form of dried biomass from *F. multivorum* cells that are fermented, stabilized with the agents described in Example 2, pasteurized to kill the cells, and dried using spray-drying. All of these preparative steps are carried out by Applied Food Biotechnology, Inc., at its facilities in O'Fallon, Mo.

All test animals will be hatched from carotenoid-deficient eggs. These are created by feeding a parental generation (designated as Pi birds) with only carotenoid-deficient feed after the birds reach maturity. Their eggs are broken open and analyzed for carotenoids until the eggs become carotenoid-deficient. Eggs which are subsequently laid by these carotenoid-deficient parental birds will be used to hatch all test and control birds.

The test and control birds are divided into four major groups, which receive different diets. These groups are designated as the C+ group, the C− group, the BC+ group, and the ZX+ group, depending on which carotenoids they receive in their diets.

Birds in the C+ group are fed a standard commercial diet which contains several carotenoids; this diet also contains synthetic alpha-tocopherol (Vitamin E) as an additive. Retinal tissue from birds which received this standard C+ diet has been analyzed to determine average baseline concentrations of a number of specific carotenoids and vitamins of interest, including zeaxanthin, lutein, β-carotene, vitamin A, and vitamin E. The baseline values for these birds are in Table 1.

Birds in the C− diet group are fed a diet which is essentially devoid of all carotenoids, as described above. However, this diet contains all other essential nutrients, and it contains synthetic vitamins A and E as additives.

Birds in the BC+ group receive a diet which is devoid of all other carotenoids, but which contains β-carotene as an additive. This will allow a direct comparison of β-carotene and zeaxanthin in protecting the retina.

Birds in the ZX+ group receive a diet which is devoid of all other carotenoids but which contains dried biomass containing the R-R isomer of zeaxanthin, from AFB's *F. multivorum* cells. There will be two different dosages of zeaxanthin fed to these birds; one ZX+ group will receive a relatively small quantity of zeaxanthin, averaging 5 mg of zeaxanthin per kilogram of feed. Since Japanese quail eat about 25 to 35 grams of food per day, this translates to about 125 to 175 micrograms of zeaxanthin per bird per day in the low dosage group. The other ZX+ group will be fed a ten-fold higher quantity, averaging 1.25 to 1.75 milligrams of zeaxanthin per bird per day. These two different dosage levels will allow a quantitative dose-and-effect relationship to be evaluated, to correlate the quantity of zeaxanthin ingested to various indicators of retinal damage. All birds which receive zeaxanthin will be in the C− diet group, so they will not be receiving any other carotenoids.

All birds will be raised and kept in normal brooding cages. Except as noted below, they will be kept under normal broad-spectrum lighting of about 200 lux intensity, 14 hours on and 10 hours off each day.

Some of the test birds will be subjected to high-intensity light at 12,000 lux for a single period, which initially will range from 2 to 8 hours for several initial groups of trial birds. This high-intensity exposure is expected generate a level of retinal damage that will be

TABLE 1

| Results: | Compound Identified | Concentration (ng per mg retina) |
|---|---|---|
| Retinal Extract of Japanese Quail (*Coturnix coturnix japonicum*) All birds were fed a standard commercial diet which contained significant quantities of β-Carotene. No β-Carotene was detected in these retinas. | Zeaxanthin | 4.7 |
| | Lutein | 4.0 |
| | alpha-Tocopherol | 15.6 |
| | gamma-Tocopherol | 5.0 |
| | Retinol (Vit. A) | 5.8 |
| | Canthaxanthin | 1.7 |
| | alpha-Cryptoxanthin | 1.4 | severe in carotenoid-deficient birds while being less severe in carotenoid-normal birds. If initial tests indicate that the level of damage is either too low or too high to be optimal for analytical purposes, the exposure period will be lengthened or shortened accordingly. The light bulbs will be behind cooling devices, to ensure that ambient temperatures do not affect the outcome. Birds will be sacrificed at various times over a 7 day period after exposure to the high-intensity lights. In addition, in each of the diet and treatment groups, various birds will be sacrificed at stages which allow evaluation of the effects of diets and treatments as a function of aging.

All retinas from sacrificed birds will be analyzed quantitatively for lutein, zeaxanthin, and other carotenoids, for vitamins A and E, and for drusen and lipofuscin deposits as indicators of macular degeneration.

Based on numerous animal tests that have been reported in the scientific literature, and based upon what is known about how carotenoids function in the retina, there is every reason to believe and anticipate that Japanese quail which are fed C− diets (i.e., carotenoid-deficient diets) will display the following symptoms in their retinas: (1) they will develop substantially higher levels of drusen and lipofuscin than birds that receive C+ diets containing carotenoids; (2) they will be more susceptible to light-induced retinal damage than birds that receive a C+ diet; and (3) the extent of the damage caused by high-intensity light exposure will be more severe in C− birds than in C+ birds. These aspects of the bird tests, which involve other carotenoids rather than zeaxanthin, will confirm what has already been established many times before in tests involving other types of animals, and they will establish numerical values for Japanese quail, which will render the zeaxanthin data more useful and meaningful.

The results from the zeaxanthin tests on these birds are expected to show the following:

1. Zeaxanthin which has been synthesized by *F. multivorum* is digested in a normal manner, crosses the intestinal barrier, and enters the bloodstream after being fed to the birds.

2. Zeaxanthin which has been synthesized by *F. multivorum* is taken up by yellow-pigmented retinal cells in the birds' eyes, in sufficient quantities to help protect retinal tissue against phototoxic damage.

3. Zeaxanthin is substantially more potent and effective than either β-carotene or vitamin E in protecting the pigmented portion of the retina against light-induced damage, as evidenced by the higher potency of zeaxanthin in preventing or reducing the quantities of drusen and/or lipofuscin in the retinas of test animals exposed for prolonged periods to high intensity blue light.

4. Although any predictions about retinal aging processes in small animals that live for only about 1 to 4 years must be qualified, zeaxanthin is expected to be able to reduce drusen and/or lipofuscin accumulation in the retinas of test animals that have not been subjected to abnormal amounts of light, but which have aged to a one-year time frame, which in Japanese quail has been shown to be sufficient for demonstrating age-related accumulation of drusen and lipofuscin.

5. There is likely to be a direct dose-response relationship between the quantity of zeaxanthin which is fed to the birds, and the amount of protection provided to the retinal tissue.

Example 6

Effects of Zeaxanthin on Mature Birds That Were Previously Deprived of Carotenoids A group of Japanese quail which have been hatched from carotenoid-deficient eggs (as described above) will be raised to maturity on a diet devoid of carotenoids. After they reach middle age (at approximately 24 weeks), their diets will be supplemented with zeaxanthin from *F. multivorum* dried biomass, for periods ranging from ½ day to 7 days, to generate dose-response data. These birds will then be divided into different treatment groups. Some groups will be exposed to high-intensity light as described above, while other groups in control populations will be kept in regular low-intensity lighting. The birds will then be sacrificed and their retinal tissue will be examined for carotenoids, vitamins, and drusen and lipofuscin deposits, to evaluate the levels of protection provided by any zeaxanthin which has entered their retinas.

This series of tests will help determine two things: (1) whether zeaxanthin supplements are capable of protecting retinal tissue, even if the nutritional supplementation is not commenced until after the animals have passed through the infant and juvenile stages and have reached maturity; and (2) the effects of zeaxanthin dosage on protection levels. It is expected that zeaxanthin supplements will be capable of helping to protect retinal tissue against phototoxic damage and age-related macular degeneration, even if the nutritional supplementation is not commenced until after the animals have reached maturity.

Thus, there has been shown and described a new and useful means for creating and using zeaxanthin preparations for human ingestion, containing the R-R stereoisomer of zeaxanthin as a sole isomer and a sole carotenoid, to prevent, treat, or otherwise reduce the damage and loss of eyesight caused by macular degeneration. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Bauernfeind, J. C. (ed.), *Carotenoids as Colorants and Vitamin A Precursors: Technological and Nutritional Applications* (Academic Press, New York, 1981)

Bone, R. A., "The role of the macular pigment in the detection of polarized light," *Vision Research* 20: 213–220 (1980)

Bone, R. A., et al, "Preliminary identification of the human macular pigment," *Vision Res.* 25: 1531–1535 (1985)

Bone, R. A., et al, "Analysis of the macular pigment by HPLC: retinal distribution and age study," *Invest. Opthalmol. Vis. Sci.* 29: 843–849 (1988)

Bone R. A., et al, "Stereochemistry of the macular carotenoids," *Invest. Ophthalmol. Vis. Sci.* 34: 2033–2040 (1993)

Bone, R. A., et al, "Distribution of macular pigment stereomers in individual eyes, including those with age-related macular degeneration (AMD)," *ARVO Abstracts: Invest. Ophthalmol. Vis. Sci.* 35: 1502 (1994)

di Mascio, P., et al, "Lycopene as the most efficient biological carotenoid singlet oxygen quencher," *Archives of Biochemistry and Biophysics* 274: 532–538 (1989)

Dorey, C. K., et al, "Lipofuscin in aged and AMD eyes," in *Retinal Degeneration* (Hollyfield et al, editors, Plenum Press, New York, 1993)

Eye Disease Case Control Study Group, "Antioxidant status and neovascular age-related macular degeneration," *Arch. Ophthalmol.* 11: 104–109 (1993)

Eye Disease Case Control Study Group, "Risk factors for neovascular age-related macular degeneration," *Arch. Ophthalmol.* 10: 1701–1708 (1992)

Foote, C. S., et al, "Chemistry of singlet oxygen. XI. Cis-Trans isomerization of carotenoids by singlet oxygen and a probable quenching mechanism," *J. Amer. Chem. Soc.* 92: 5218–5219 (1970)

Foote, C. S., et al, "Chemistry of singlet oxygen. X. Carotenoid quenching parallels biological protection," *J. Amer. Chem. Soc.* 92: 5216–5218 (1970)

Gerster, H., "Review: antioxidant protection of the ageing macula," *Age and Aging* 20: 60–69 (1991)

Gittinger, J. W., *Manual of Clinical and Problem Ophthalmology* (Little-Brown, Boston, 1988)

Haegerstrom-Portnoy, G., "Short-wavelength-sensitive-cone sensitivity loss with aging: a protective role for macular pigment?," *J. Opt. Soc. Am.* A5: 2140–2144 (1988)

Ham, W. T., Jr., et al, "Basic mechanisms underlying the production of photochemical lesions in the mammalian retina," *Current Eye Research* 3: 165–174 (1984)

Handelman, G. J. and Dratz, E. A., "The role of antioxidants in the retina and retinal pigment epithelium and the nature of prooxidant-induced damage," *Adv. in Free Radical Biology & Medicine* 2: 1–89 (1986)

Handelman, G. J., et al, "Carotenoids in the human macula and whole retina," *Invest. Ophthalmol. Vis. Sci.* 29: 850–855 (1988)

Jialal, I., et al, "β-Carotene inhibits the oxidative modification of low-density lipoprotein," *Biochimica et Biophysica Acta* 1086: 134–138 (1991)

Khachik, F., et al, "Separation, identification and quantification of carotenoids in fruits, vegetables and human plasma by high performance liquid chromatography," *Pure and Applied Chemistry* 63: 71–80 (1991)

Kirschfeld, K., "Carotenoid pigments: their possible role in protecting against photooxidation in eyes and photoreceptor cells," *Proc. R. Soc. Lond. B* 216: 71–85 (1982)

Malinow, M. R., et al, "Diet-related macular anomalies in monkeys," *Invest. Ophthalmol. Vis. Sci.* 19: 857–863 (1980)

Pease, P. L., et al. "Optical density of human macular pigment." *Vision Res.* 27: 705–710 (1987)

Peto, R., et al. "Can dietary beta-carotene materially reduce human cancer rates?" *Nature* 290: 201–208 (1981)

Schalch, W., "Carotenoids in the retina—a review of their possible role in preventing or limiting damage caused by light and oxygen." *EXS* 62: 280–298 (1992)

Seddon, J. M., et al. "Dietary carotenoids, vitamins A, C, and E, and advanced age-related macular degeneration." *JAMA* 272: 1413–1420 (1994)

Snodderly, D. M., et al. "The macular pigment. I. Absorbance spectra, localization, and discrimination from other yellow pigments in primate retinas." *Invest. Ophthalmol. Vis. Sci.* 25: 660–673 (1984)

Sperduto, R. D., et al. "Do we have a nutritional treatment for age-related cataract or macular degeneration?." *Arch. Ophthalmol.* 108: 1403–1405 (1990)

Taylor, A., et al. "Oxidation and aging: impact on vision." *Journal of Toxicology and Industrial Health* 9: 349–371 (1993)

Vaughn, D. and Asbury, T., *General Ophthalmology*, 13th ed. (Appleton and Lange, Norwalk, Conn., 1992)

Wald, G., "The photochemistry of vision." *Doc. Ophthalmol.* 3: 94 (1949)

Weiter, J. J., et al. "Central sparing in annular macular degeneration." *Am. J. Ophthalmol.* 106: 286–292 (1988)

Werner, J. S., et al. "Aging and human macular pigment density." *Vision Res.* 27: 257–268 (1987)

We claim:

1. A method for treating macular degeneration in humans, comprising the step of administering, to a human patient who has been diagnosed as suffering from macular degeneration, a drug formulation which contains a 3R-3'R stereoisomer of zeaxanthin in a carrier substance which is suited for administration to humans, and which does not contain a substantial quantity of other undesired stereoisomers of zeaxanthin, wherein the 3R-3'R stereoisomer of zeaxanthin is present in a sufficient quantity to provide a therapeutic benefit in a human suffering from macular degeneration.

2. The method of claim 1 wherein zeaxanthin is present at a concentration of at least about two percent, by weight, of the drug formulation.

3. The method of claim 1 wherein at least about 3 milligrams of zeaxanthin per day is administered to the patient.

4. The method of claim 1 wherein the 3R-3'R stereoisomer of zeaxanthin constitutes at least about 90 percent of all zeaxanthin in the drug formulation while undesired S-S and S-R stereoisomers constitute less than about 10 percent of all zeaxanthin in the drug formulation.

5. The method of claim 4 wherein the drug formulation is characterized by an absence of any significant quantity of undesired S-S and R-S stereoisomers of zeaxanthin, and wherein the 3R-3'R stereoisomer of zeaxanthin is present as a sole detectable stereoisomer of zeaxanthin.

6. The method of claim 1 wherein the 3R-3'R stereoisomer of zeaxanthin constitutes at least about 90 percent of total carotenoids in the drug formulation, and wherein other carotenoids which might compete against zeaxanthin for alimentary uptake or tissue deposition after ingestion constitute less than about 10 percent, by weight, of total carotenoids in the drug formulation.

7. The method of claim 1 wherein the 3R-3'R stereoisomer of zeaxanthin is synthesized by culturing, under suitable conditions which promote zeaxanthin biosynthesis, bacterial cells descended from a strain of *Flavobacterium multivorum* which has been given ATCC accession number 55238.

8. The method of claim 1 wherein the desired 3R-3'R stereoisomer of zeaxanthin is synthesized by culturing, under suitable conditions which promote zeaxanthin biosynthesis, cells which have been genetically engineered to contain at least one zeaxanthin-synthesis gene containing a DNA sequence obtained from cells descended from a strain of *Flavobacterium multivorum* which has been given ATCC accession number 55238.

9. A method for treating a human patient who has a genetic susceptibility to a macular degenerative disease, comprising the step of administering, to a human patient who has been diagnosed as having a genetic susceptibility to macular degeneration, a drug formulation comprising a 3R-3'R stereoisomer of zeaxanthin in a suitable carrier substance which does not contain a substantial quantity of any other undesired stereoisomer of zeaxanthin.

10. The method of claim 9 wherein the patient suffers from a genetic defect which contributes to a disease selected from the group consisting of Stargardt's disease, Best's disease, Batten's disease, Sjogren-Larsson syndrome, cone-rod dystrophy, ovine ceroid lipofuscinosis, and diseases which involve lysosomal storage problems.

11. A method of reducing a future risk of age-related macular degeneration in humans, comprising the step of periodically orally ingesting a nutritional supplement containing a 3R-3'R stereoisomer of zeaxanthin in a carrier substance which is suited for ingestion by humans and which does not contain a substantial quantity of any other stereoisomer of zeaxanthin, wherein the nutritional supplement contains at least about 0.5 milligrams of the 3R-3'R stereoisomer of zeaxanthin in each dosage, and wherein the 3R3'R stereoisomer of zeaxanthin constitutes at least about 90 percent of all zeaxanthin in the nutritional supplement while undesired S-S and S-R stereoisomers constitute less than about 10 percent of all zeaxanthin in the nutritional supplement.

12. The method of claim 11 wherein the nutritional supplement is characterized by an absence of any significant quantity of undesired S-S and R-S stereoisomers of zeaxanthin, and wherein the 3R-3'R stereoisomer of zeaxanthin is present in the nutritional supplement as a sole detectable stereoisomer of zeaxanthin.

13. The method of claim 11 wherein the 3R-3'R stereoisomer of zeaxanthin is synthesized by culturing, under suitable conditions which promote zeaxanthin biosynthesis, bacterial cells descended from a strain of *Flavobacterium multivorum* which has been given ATCC accession number 55238.

14. The method of claim 11 wherein the desired 3R-3'R stereoisomer of zeaxanthin is synthesized by culturing, under suitable conditions which promote zeaxanthin biosynthesis, cells which have been genetically engineered to contain at least one zeaxanthin-synthesis gene containing a DNA sequence obtained from cells descended from a strain of *Flavobacterium multivorum* which has been given ATCC accession number 55238.

* * * * *